(12) United States Patent
Clary et al.

(10) Patent No.: US 11,731,973 B2
(45) Date of Patent: Aug. 22, 2023

(54) SUBSTITUTED PYRAZOLO[3,4-D]PYRIMIDINES AS MTOR INHIBITORS

(71) Applicant: GALDERMA RESEARCH & DEVELOPMENT, Biot (FR)

(72) Inventors: Laurence Clary, La Colle sur Loup (FR); Jean-François Fournier, Antibes (FR); Gilles Ouvry, Biot (FR); Yushma Bhurruth-Alcor, Ashburn, VA (US); Etienne Thoreau, Saint Vallier de Thiey (FR); Loïc Tomas, La-Tour-de-Peilz (CH)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 16/907,154

(22) Filed: Jun. 19, 2020

(65) Prior Publication Data

US 2020/0317679 A1 Oct. 8, 2020

Related U.S. Application Data

(63) Continuation of application No. PCT/EP2018/086066, filed on Dec. 20, 2018.

(51) Int. Cl.
 *A61K 31/519* (2006.01)
 *C07D 487/04* (2006.01)
 *C07D 519/00* (2006.01)
 *A61K 9/00* (2006.01)

(52) U.S. Cl.
 CPC .......... *C07D 487/04* (2013.01); *A61K 9/0014* (2013.01); *C07D 519/00* (2013.01)

(58) Field of Classification Search
 CPC .................... A61K 31/519; C07D 487/04
 USPC ........................ 514/262.1; 544/262
 See application file for complete search history.

(56) References Cited

FOREIGN PATENT DOCUMENTS

| EP | 2 705 181 B1 | 3/2014 |
|---|---|---|
| JP | 2009-519222 A | 5/2009 |
| JP | 2014-513138 A | 5/2014 |
| JP | 2014-513141 A | 5/2014 |
| JP | 2016-537367 A | 12/2016 |
| WO | WO-2005/028434 A2 | 3/2005 |
| WO | WO-2007/061737 A2 | 5/2007 |
| WO | WO-2009/062118 A2 | 5/2009 |
| WO | WO-2009/114874 A2 | 9/2009 |
| WO | WO-2009/117482 | 9/2009 |
| WO | WO-2012/148540 A1 | 11/2012 |
| WO | WO-2012/154695 A2 | 11/2012 |
| WO | WO-2015/074135 A1 | 5/2015 |
| WO | WO-2015/157125 A1 | 10/2015 |
| WO | WO-2019122059 A1 * | 6/2019 ........... C07D 519/00 |

OTHER PUBLICATIONS

Jordan, V. C. Nature Reviews: Drug Discovery, 2, 2003, 205.*
Hackam, et al. JAMA, 296(14), 2006, 1731-1732.*
Buerger, Claudia, et al., "Blocking mTOR Signalling with Rapamycin Ameliorates Imiquimod-induced Psoriasis in Mice," Journal Compliation, Acta Dermato-Venereologica 2017; 97: 1087-1094, doi: 10.2340/00015555-2724.
International Search Report dated Mar. 11, 2019 received in corresponding International Application No. PCT/EP2018/086066 (2 pages).
International Search Report dated Mar. 27, 2019 received in corresponding International Application No. PCT/EP2018/086074 (3 pages).
Stout et al., "High-Throughput tructural Biology in Drug Discovery: Protein Kinases", Current Pharmaceutical Design, 10(10), (2004), pp. 1069-1082.
Yang et al., "Topical application of rapamyoin ointment ameliorates Dermatophagoides farina body extract-induced atopic dermatitis in NC/NGA mice", Experimental Dermatology, vol. 23, Jun. 3, 2014, pp. 568-572.
Yuan et al., "PF-04691502, a Potent and Selective Oral Inhibitor of PI3K and mTOR Kinases with Antitumor Activity", Molecular Cancer Therapeutics, vol. 10, No. 11, Jul. 12, 2011, pp. 2189-2199.

* cited by examiner

*Primary Examiner* — Douglas M Willis
(74) *Attorney, Agent, or Firm* — Sunit Talapatra; Foley & Lardner LLP

(57) ABSTRACT

The invention relates to novel mTOR inhibitor compounds having the formula (I) or a pharmaceutically acceptable salt thereof, compositions comprising the mTOR inhibitor compounds, methods for producing the same, and the use thereof.

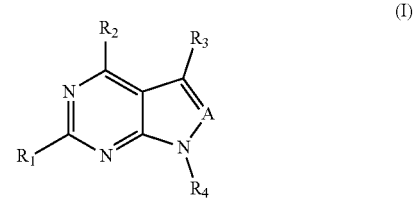

(I)

17 Claims, 7 Drawing Sheets

SUBSTITUTED PYRAZOLO[3,4-D]PYRIMIDINES AS MTOR INHIBITORS

CROSS-REFERENCE TO RELATED APPLICATIONS

This application is a continuation of International Application No. PCT/EP2018/086066 filed Dec. 20, 2018, which claims the benefit of and priority to FR Application No. 1771407 filed Dec. 21, 2017, both of which are hereby incorporated by reference herein in their entireties.

FIELD OF INVENTION

The present invention relates to novel compounds which inhibit the serine/threonine kinase mTOR ("mechanistic target of rapamycin", also known as FRAP, RAFT, RAPT and SEP). The invention also relates to compositions comprising same, to processes for preparing same and to the uses thereof in compositions as medicament.

BACKGROUND OF THE INVENTION

The protein kinase mTOR is the catalytic center of two functionally distinct multiprotein complexes, conserved in all eukaryotes and named mTORC1 and mTORC2 (Dunlop et al., "Mammalian target of rapamycin complex 1: signalling inputs, substrates and feedback mechanisms", 2009; Guertin et al., "The pharmacology of mTOR inhibition", 2009). When it is associated with Raptor (regulatory associated protein of TOR) and with mLST8 (mammalian lethal with sec13 protein 8), mTOR forms the complex mTORC1. This complex interacts with Deptor (DEP domain-containing mTOR-interacting protein), FKBP38 and PRAS40 (proline-rich Akt substrate of 40 kDa), which are down-regulators of mTORC1. To form mTORC2, mTOR interacts with the proteins Rictor (rapamycin-insensitive companion of TOR), Sin1 (stress-activated map kinase-interacting protein 1) and mLST8. Furthermore, mTORC2 also becomes associated with Deptor, which represses its activity, and also with PPR5/Protor, the function of which remains unknown. When it is bound to FKBP12, rapamycin specifically inhibits mTORC1.

mTOR is notably known for regulating cell proliferation, cell growth, cell mobility, cell survival, protein biosynthesis and transcription.

It has been shown that disruptions of the mTOR signaling pathway are the cause of several diseases, in particular various types of cancer and multiple hamartomas.

Patent WO 2007/061737, which discloses mTOR-inhibiting bicyclic compounds, is known, for example. They are used in cancer treatment, such as breast cancer, lung cancer, non-small-cell lung cancer, kidney cancer, renal carcinoma, prostate cancer, blood cancer, liver cancer, ovarian cancer, thyroid cancer, endometrial cancer, lymphoma, renal cell carcinoma, or mantle cell lymphoma.

Patent WO 2009/117482 is also known, which more particularly describes salts and other polymorphs of mTOR-inhibiting bicyclic compounds, also used in cancer treatment, of the same type as those described in WO 2007/061737.

Rapamycin, an mTOR inhibitor, has been known for a long time for its immunosuppressant properties. It has, nevertheless, shown limited therapeutic success when it is administered systemically to patients suffering from psoriasis. Also, recent data have shown that the mTOR signaling pathway is hyperactivated in lesional psoriatic skin, which may contribute toward the disease by interfering with keratinocyte maturation. The effect of topical treatment with rapamycin in a model of imiquimod-induced psoriatic mice was studied (Bürger et al., "Blocking mTOR Signalling with Rapamycin Ameliorates Imiquimod-induced Psoriasis in Mice", 2017). The immunohistological analysis revealed that rapamycin not only prevented activation of the mTOR signaling pathway (levels of P-mTOR and of P-S6), but almost normalized the expression of the epidermal differentiation markers. In addition, the influx of innate immune cells into the draining lymphatic ganglions was partially reduced by treatment with rapamycin. These data emphasize the role of the mTOR signaling pathway in the pathogenesis of psoriasis, and support the study of the topical inhibition of mTOR as a novel anti-psoriasis strategy.

SUMMARY OF THE INVENTION

There is thus a real need to develop treatments, in particular topical treatments, for patients suffering from diseases such as psoriasis.

Taking the foregoing into account, one problem that the invention proposes to solve is that of proposing novel mTOR inhibitors notably for improving the treatment of immune-mediated proliferative or inflammatory skin diseases.

The Applicant has developed novel mTOR-inhibiting compounds.

One aspect of the present invention is thus an mTOR-inhibiting compound of general formula (I)

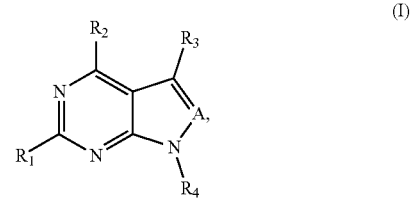

or a pharmaceutically acceptable salt thereof, in which each variable is as defined and described hereinbelow.

An aspect of the invention is also a composition comprising, in a physiologically acceptable medium, an mTOR-inhibiting compound of formula (I) according to the invention or a pharmaceutically acceptable salt thereof. It is intended to be used as a medicament, in particular in the treatment of diseases involving an mTOR enzyme with serine-threonine kinase activity and notably in the treatment of dermatological complaints associated with a keratinization disorder with a proliferative, inflammatory and/or immunoallergic component, such as psoriasis, atopic dermatitis, actinic keratosis or acne, preferably atopic dermatitis, more preferably the inflammatory component of atopic dermatitis and even more preferably topical treatment of the inflammatory component of atopic dermatitis.

BRIEF DESCRIPTION OF THE DRAWINGS

The invention will be better understood on reading the nonlimiting description which follows, which has been drafted with regard to the attached drawings, in which.

Figure 1:
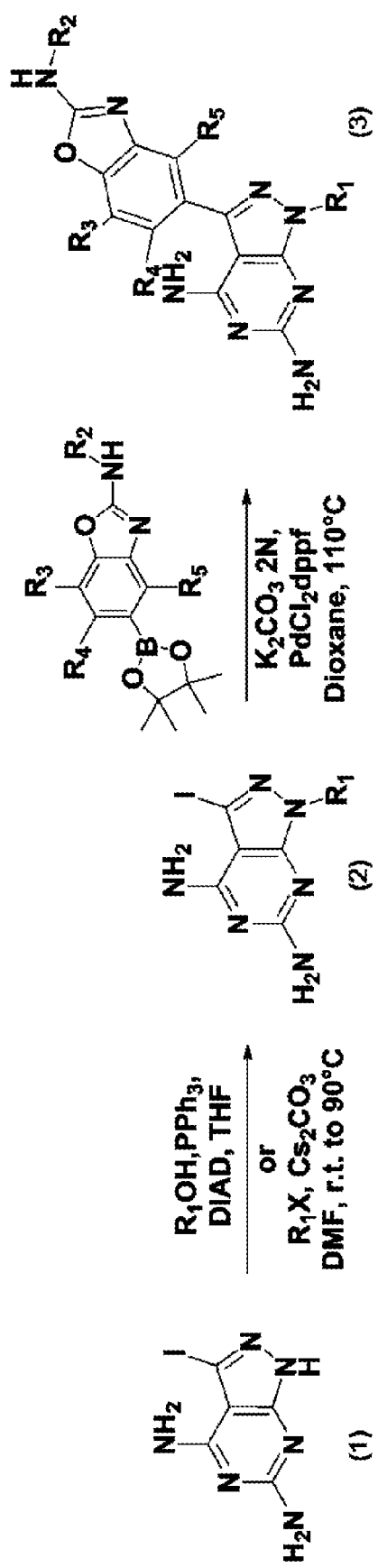
FIG. 1 represents a route for synthesizing the compound 3-(2-aminobenzoxazol-5-yl)-1-((S)-1,3-dimethylbutyl)-1H-pyrazolo[3,4-d]pyrimidine-4,6-diamine (example 1)

The present invention relates to novel mTOR-inhibiting compounds or a pharmaceutically acceptable salt thereof.

The term "mTOR inhibitor" refers to compounds which down-regulate, i.e. reduce, block or even suppress, the activation of the mTOR signaling pathway, by competing, advantageously selectively, with the substrates at the level of mTORC1 and/or mTORC2 or by modifying the active site of these enzymes which can thus no longer catalyze a given substrate. The terms (mTOR) "antagonist" and (mTOR) "inhibitor" are used without preference according to the present invention.

The compounds according to the invention may be represented by the general formula (I)

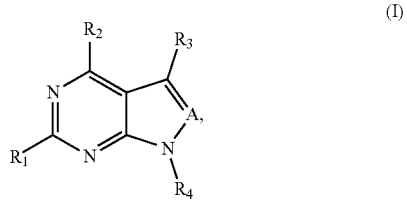

(I)

or a pharmaceutically acceptable salt thereof, in which $R_1$ represents an —$NH_2$, —NHMe or —NHEt radical;

$R_2$ represents a hydrogen atom, a halogen atom chosen from F, Cl, Br and I, an —$NH_2$, —NHalkyl, —NHAc, nitrile, methyl (Me), ethyl (Et), trifluoromethyl, —OH or methoxy radical;

it being understood that when $R_2$ is other than an —$NH_2$ radical, then $R_1$ represents an —$NH_2$ radical;

$R_3$ represents a simple or fused bicyclic aromatic or heteroaromatic radical, which is unsubstituted or mono- or polysubstituted with one or more radicals chosen from a halogen atom chosen from F, Cl, Br and I, —$NHR_5$, nitrile, methyl, ethyl, trifluoromethyl, —$OR_6$;

with $R_5$ representing a hydrogen atom, a radical from among cyclopropyl, acyl, saturated or unsaturated $C_1$-$C_6$ alkyl, optionally interrupted with a heteroatom O or S, and unsubstituted or substituted with a $C_3$-$C_5$ cycloalkyl or heterocycloalkyl; and with $R_6$ representing a hydrogen atom or a methyl radical;

$R_4$ represents a hydrogen atom, a linear or branched $C_1$-$C_{10}$ alkyl radical, a saturated or unsaturated $C_3$-$C_{10}$ ring or bicycle, optionally interrupted with one or more heteroatoms O, S and N, and unsubstituted or substituted with a radical from among sulfone, fluoro, cyano, ester, —$NR_7$, —$NR_7R_8$, $C_3$-$C_6$ cycloalkyl or heterocycloalkyl, or an aromatic ring or a heterocycle which is unsubstituted or mono- or polysubstituted with a halogen atom chosen from Cl and F or a radical from among —OH, —OMe, trifluoromethyl, methyl, ethyl, —$NH_2$, —NHMe, —$NMe_2$, with $R_7$ and $R_8$ representing, independently of each other, a hydrogen atom, a $C_1$-$C_3$ alkyl, cyclopropyl or acyl radical, or together forming a $C_3$-$C_5$ ring; and A represents a —CH radical or a nitrogen atom.

According to the present invention, the term "alkyl" means a linear or branched radical containing, for example, from 1 to 6 ($C_1$-$C_6$) or from 1 to 3 ($C_1$-$C_3$) carbon atoms, advantageously methyl, ethyl, propyl, isopropyl, butyl, tert-butyl, 2-methylbutyl, pentyl, 2-methylpentyl or hexyl radicals.

The term "acyl" means a radical obtained by removing the hydroxyl group from a carboxylic acid; the acyl group corresponding to a carboxylic acid of formula —RCOOH will have the formula —RCO, in which the carbon atom and the oxygen atom are linked via a double bond (carbonyl group).

The term "cycloalkyl" means a cycloalkyl radical containing from 3 to 6 carbon atoms advantageously chosen from cyclopropyl, cyclobutyl, cyclopentyl and cyclohexyl.

The term "heterocycloalkyl" or "heterocycle" means, for example, a piperidino, morpholino, pyrrolidino or piperazino radical.

The term "aromatic ring" means a flat cyclic radical containing (4n+2) delocalized electrons, n being the number of rings constituting the radical; if the ring contains elements other than carbon and hydrogen, it is referred to as an aromatic heterocycle or a heteroaryl group.

When the compounds according to the invention are in the form of a pharmaceutically acceptable salt, it is preferably a salt obtained from a nontoxic base or acid.

The term "pharmaceutically acceptable salt" refers to salts which are, in the context of good medical judgement, suitable for use in contact with human and lower animal tissues without excessive toxicity, irritation, allergic response and the like and are commensurate with a reasonable benefit/risk ratio. Pharmaceutically acceptable salts are well known in the prior art. The pharmaceutically acceptable salts of the compounds of the present invention comprise those derived from suitable inorganic and organic acids and bases.

When the compound of the present invention is acidic, its corresponding salt may be prepared from pharmaceutically acceptable nontoxic bases, comprising inorganic bases and organic bases.

The salts derived from these inorganic bases comprise aluminum, ammonium, calcium, copper, iron, lithium, magnesium, manganese, potassium, sodium and similar salts. The ammonium, calcium, magnesium, potassium and sodium salts are particularly preferred.

The salts derived from pharmaceutically acceptable nontoxic organic bases comprise salts of primary, secondary and tertiary amines, and also of cyclic amines and of substituted amines such as naturally substituted and synthesized amines.

Other pharmaceutically acceptable nontoxic organic bases from which salts may be formed comprise ion-exchange resins, for instance arginine, betaine, caffeine, choline, N',N'-dibenzylethylenediamine, diethylamine, 2-diethylaminoethanol, 2-dimethylaminoethanol, ethanolamine, N,N-diethylethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt may be prepared from pharmaceutically acceptable nontoxic acids, comprising inorganic acids and organic acids.

Such acids comprise, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric or p-toluenesulfonic acid and the like. Citric, hydrobromic, hydrochloric, maleic, phosphoric, sulfuric and tartaric acid are particularly preferred.

DESCRIPTION OF EMBODIMENTS

According to one embodiment of the invention, the pharmaceutically acceptable salt is chosen from tromethamine, sodium, calcium and L-arginine.

According to another embodiment of the invention, the salt is chosen from magnesium, potassium, N,N-diethylethanolamine, N-methyl-D-glucamine and piperazine.

In certain embodiments, the salt is in hydrate or solvate salt form.

In certain embodiments, the salt is substantially in amorphous form.

In certain embodiments, the salt is essentially in crystalline form.

In certain embodiments, the salt is crystalline to at least about 95% by weight.

In certain embodiments, the salt is substantially in single crystalline form.

According to the present invention, the preferred compounds are those of general formula (I)

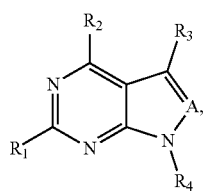

(I)

or a pharmaceutically acceptable salt thereof, in which
$R_1$ represents an —$NH_2$ radical;
$R_2$ represents a halogen atom chosen from F, Cl, Br and I, or an —$NH_2$ radical;
$R_3$ represents a fused bicyclic heteroaromatic radical, which is unsubstituted or mono- or polysubstituted with one or more radicals chosen from a halogen atom chosen from F, Cl, Br and I, —$NHR_5$, nitrile, methyl, ethyl, trifluoromethyl, —$OR_6$;
  with $R_5$ representing a hydrogen atom, a radical from among cyclopropyl, acyl, saturated or unsaturated $C_1$-$C_6$ alkyl, optionally interrupted with a heteroatom O or S, and unsubstituted or substituted with a $C_3$-$C_5$ cycloalkyl or heterocycloalkyl; and
  with $R_6$ representing a hydrogen atom or a methyl radical;
$R_4$ represents a branched $C_3$-$C_{10}$ alkyl radical, a $C_3$-$C_{10}$ ring or bicycle, optionally interrupted with a heteroatom O or S, and unsubstituted or substituted with one or more radicals chosen from fluoro and $C_3$-$C_6$ cycloalkyl or heterocycloalkyl; and
A represents a nitrogen atom.

The compounds that are more preferred according to the invention are those of general formula (I), or a pharmaceutically acceptable salt thereof, in which:
$R_1$ represents an —$NH_2$ radical;
$R_2$ represents a Cl atom or an —$NH_2$ radical;
$R_3$ represents a fused bicyclic heteroaromatic radical, which is mono- or polysubstituted with one or more radicals chosen from a halogen atom chosen from F, Cl, Br and I, —$NHR_5$, nitrile, methyl, ethyl, trifluoromethyl, —$OR_6$;
  with $R_5$ representing a hydrogen atom, a radical from among cyclopropyl, acyl, saturated or unsaturated $C_1$-$C_6$ alkyl, optionally interrupted with a heteroatom O or S, and unsubstituted or substituted with a $C_3$-$C_5$ cycloalkyl or heterocycloalkyl; and
  with $R_6$ representing a hydrogen atom or a methyl radical;
$R_4$ represents a branched $C_3$-$C_{10}$ alkyl radical, a $C_3$-$C_{10}$ ring or bicycle, optionally interrupted with a heteroatom O or S, and unsubstituted or substituted with one or more radicals chosen from fluoro and $C_3$-$C_6$ cycloalkyl or heterocycloalkyl; and
A represents a nitrogen atom.

According to the present invention, the compounds that are even more preferred are those of formula (Ia),

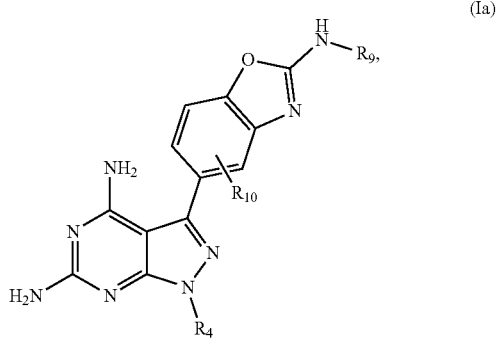

(Ia)

or a pharmaceutically acceptable salt thereof, in which:
$R_4$ represents a branched $C_3$-$C_{10}$ alkyl radical, a $C_3$-$C_{10}$ ring or bicycle, optionally interrupted with a heteroatom O or S, and unsubstituted or substituted with one or more radicals chosen from fluoro and $C_3$-$C_6$ cycloalkyl or heterocycloalkyl;
$R_9$ represents a hydrogen atom or a methyl or ethyl radical; and
one or more $R_{10}$, taken independently, represent a hydrogen atom, a halogen atom chosen from Cl and F, or an —OH, methyl or —OMe radical.

More preferably, the compounds of formula (I) or (Ia) or a pharmaceutically acceptable salt thereof are those in which:
$R_4$ represents a branched $C_3$-$C_{10}$ alkyl;
$R_9$ represents a hydrogen atom; and one or more $R_{10}$, taken independently, represent a hydrogen atom, a halogen atom chosen from Cl and F, or a methyl radical.

Even more preferably, the compounds of formula (I) or (Ia) or a pharmaceutically acceptable salt thereof are those in which:

$R_4$ represents a branched $C_4$-$C_6$ alkyl;
$R_9$ represents a hydrogen atom; and
$R_{10}$ represents a hydrogen or fluorine atom.

The particularly preferred compounds of formula (I) or (Ia) or a pharmaceutically acceptable salt thereof are those in which:

$R_4$ represents an (S)-1,3-dimethylbutyl radical;
$R_9$ represents a hydrogen atom; and
$R_{10}$ represents a hydrogen atom.

Among the compounds of formula (I) or (Ia) which fall within the context of the present invention, mention may notably be made of the following compounds:

3-(2-aminobenzoxazol-5-yl)-1-((S)-1,3-dimethylbutyl)-1H-pyrazolo[3,4-d]pyrimidine-4,6-diamine;
3-(2-amino-6-fluorobenzoxazol-5-yl)-1-((S)-1,3-dimethylbutyl)-1H-pyrazolo[3,4-d]pyrimidine-4,6-diamine;
3-(2-amino-4-fluorobenzoxazol-5-yl)-1-(1-methylcyclobutylmethyl)-1H-pyrazolo[3,4-d]pyrimidine-4,6-diamine;
3-(2-amino-6-fluorobenzoxazol-5-yl)-1-(1-methylcyclobutylmethyl)-1H-pyrazolo[3,4-d]pyrimidine-4,6-diamine;
3-(2-amino-4-fluorobenzoxazol-5-yl)-1-((S)-1,3-dimethylbutyl)-1H-pyrazolo[3,4-d]pyrimidine-4,6-diamine;
N-(5-(4,6-diamino-1-(2,2-dimethylbutyl)-1H-pyrazolo[3,4-d]pyrimidin-3-yl)benzo[d]oxazol-2-yl)acetamide;
3-(2-aminobenzoxazol-5-yl)-1-(2,2-dimethylpropyl)-1H-pyrazolo[3,4-d]pyrimidine-4,6-diamine;
3-(2-aminobenzoxazol-5-yl)-1-(2,2-dimethylbutyl)-1H-pyrazolo[3,4-d]pyrimidine-4,6-diamine;
3-(2-aminobenzoxazol-5-yl)-1-(3-methylthietan-3-ylmethyl)-1H-pyrazolo[3,4-d]pyrimidine-4,6-diamine;
3-(2-amino-4-fluorobenzoxazol-5-yl)-1-(2,2-dimethylbutyl)-1H-pyrazolo[3,4-d]pyrimidine-4,6-diamine;
1-(2,2-dimethylpropyl)-3-(2-ethylaminobenzoxazol-5-yl)-1H-pyrazolo[3,4-d]pyrimidine-4,6-diamine;
3-(2-aminobenzoxazol-5-yl)-1-(2,2-dimethylbut-3-enyl)-1H-pyrazolo[3,4-d]pyrimidine-4,6-diamine;
(+)-3-(2-aminobenzoxazol-5-yl)-1-((S)-2-methyl-2-tetrahydrofuran-2-ylpropyl)-1H-pyrazolo[3,4-d]pyrimidine-4,6-diamine;
3-(2-aminobenzoxazol-5-yl)-1-(2,2-dimethylbut-3-ynyl)-1H-pyrazolo[3,4-d]pyrimidine-4,6-diamine;
3-[4,6-diamino-3-(2-aminobenzoxazol-5-yl)pyrazolo[3,4-d]pyrimidin-1-yl]-2,2-dimethylpropan-1-ol;
3-(2-aminobenzoxazol-5-yl)-1-(2-methyl-2-methylsulfinylpropyl)-1H-pyrazolo[3,4-d]pyrimidine-4,6-diamine;
3-(2-amino-4-chlorobenzoxazol-5-yl)-1-(2,2-dimethylpropyl)-1H-pyrazolo[3,4-d]pyrimidine-4,6-diamine;
3-(2-amino-6-methoxybenzoxazol-5-yl)-1-(2,2-dimethylpropyl)-1H-pyrazolo[3,4-d]pyrimidine-4,6-diamine;
2-[4,6-diamino-1-(2,2-dimethylpropyl)-1H-pyrazolo[3,4-d]pyrimidin-3-yl]-1H-pyrrolo[2,3-b]pyridin-5-ol;
3-(2-amino-6-methoxybenzoxazol-5-yl)-1-(2,2-dimethylbutyl)-1H-pyrazolo[3,4-d]pyrimidine-4,6-diamine;
3-(2-aminobenzoxazol-5-yl)-1-isopropyl-1H-pyrazolo[3,4-d]pyrimidine-4,6-diamine;
3-(2-aminobenzoxazol-5-yl)-1-(2-ethyl-2-methanesulfonylbutyl)-1H-pyrazolo[3,4-d]pyrimidine-4,6-diamine;
3-(2-aminobenzoxazol-5-yl)-4-chloro-1-isobutyl-1H-pyrazolo[3,4-d]pyrimidin-6-ylamine;
3-(2-aminobenzoxazol-5-yl)-1-isopropyl-1H-pyrazolo[3,4-d]pyrimidin-6-ylamine;
3-(2-amino-6-chlorobenzoxazol-5-yl)-1-((S)-1,2-dimethylpropyl)-1H-pyrazolo[3,4-d]pyrimidine-4,6-diamine;
3-(2-aminobenzoxazol-5-yl)-1-isopropyl-N*6*-methyl-1H-pyrazolo[3,4-d]pyrimidine-4,6-diamine;
5-(6-amino-4-methyl-1-neopentyl-1H-pyrazolo[3,4-d]pyrimidin-3-yl)benzo[d]oxazol-2-amine;
3-(2-cyclopropylaminobenzoxazol-5-yl)-1-isopropyl-1H-pyrazolo[3,4-d]pyrimidine-4,6-diamine;
3-(2-amino-7-methyl-benzoxazol-5-yl)-1-(2,2-dimethylbutyl)-1H-pyrazolo[3,4-d]pyrimidine-4,6-diamine;
3-(2-aminobenzoxazol-5-yl)-1-(1-methylcyclobutylmethyl)-1H-pyrazolo[3,4-d]pyrimidine-4,6-diamine;
5-(6-amino-4-chloro-1-isopropyl-1H-pyrazolo[3,4-d]pyrimidin-3-yl)benzo[d]oxazol-2-amine.

An aspect of the present invention is also a composition comprising, in a physiologically acceptable medium, a compound of formula (I) or (Ia) according to the invention as defined above or a pharmaceutically acceptable salt thereof.

A pharmaceutically acceptable medium denotes a medium that is compatible with and suitable for use in contact with human and animal cells, in particular with the skin, mucous membranes and/or the integuments, without undue toxicity, irritation or allergic response or the like, and commensurate with a reasonable benefit/risk ratio.

A pharmaceutically acceptable medium according to the invention may comprise any known adjuvant used in the pharmaceutical field, which is compatible with the mTOR-inhibiting compounds according to the invention.

Nonlimiting examples that may be mentioned include solvents, buffers, aromatizing agents, binders, chelating agents, surfactants, thickeners, lubricants, gellants, humectants, moisturizers, preserving agents, antioxidants, calmative agents, pro-penetrating agents, colorants, fragrances and the like, or a mixture thereof.

Needless to say, a person skilled in the art will take care to select the optional compound(s) to be added to these compositions such that the advantageous properties intrinsically associated with the present invention are not, or are not substantially, adversely affected by the envisaged addition. Their concentration is also chosen so that they do not harm the advantageous properties of the compounds according to the invention.

The compound according to the present invention and the composition comprising same may be administered orally, rectally, topically or parenterally (subcutaneously, intramuscularly or intravenously). They are preferably administered orally or topically, more preferably topically.

The compositions according to the invention may be in liquid, solid or gas form.

Via the oral route, the composition may be in the form of tablets, gel capsules, coated tablets, syrups, suspensions, solutions, powders, granules, emulsions, suspensions of microspheres or nanospheres or lipid or polymeric vesicles allowing controlled release.

Via the parenteral route, the composition may be in the form of solutions or suspensions for perfusion or for injection.

Preferably, the pharmaceutical composition is conditioned in a form that is suitable for topical application.

Via the topical route, the compositions, which are thus more particularly intended for treating the skin and mucous membranes, may be in liquid, pasty or solid form, and more particularly in the form of ointments, creams, milks, pomades, powders, impregnated pads, syndets, solutions, gels, sprays, mousses, lotions, suspensions, sticks, shampoos or washing bases. They may also be in the form of suspensions of microspheres or nanospheres or lipid or polymeric vesicles, or of polymeric or gelled patches, or of hydrogels allowing controlled release of the active compounds. These topical compositions may moreover be either in anhydrous form or in an aqueous form.

The composition according to the invention preferably comprises between 0.001% and 5% of said compound of formula (I) or (Ia) or a pharmaceutically acceptable salt thereof, by weight relative to the total weight of the composition.

The amount effectively administered to be used according to the invention depends on the desired therapeutic effect, and may thus vary within a wide range. A person skilled in the art, in particular a medical practitioner, can readily, on the basis of his general knowledge, determine the appropriate amounts.

The composition according to the invention may comprise at least one other active ingredient.

The additional active ingredient is preferably chosen from the group comprising, but without being limited thereto, antibiotics, antibacterials, antivirals, antiparasitic agents, antifungal agents, anesthetics, analgesics, antiallergic agents, retinoids, free-radical scavengers, antipruriginous agents, antihistamines, immunosuppressants, corticosteroids, keratolytic agents, intravenous immunoglobulins, antiangiogenic agents, antiinflammatory agents and/or a mixture thereof.

More preferably, the additional active ingredient is known for its efficacy in treating dermatological complaints associated with a keratinization disorder with a proliferative, inflammatory and/or immunoallergic component, such as psoriasis, atopic dermatitis, actinic keratosis or acne.

The present invention relates to novel mTOR-inhibiting compounds of formula (I) or (Ia).

Thus, one aspect of the present invention is the compounds of formula (I) or (Ia) as described above which are intended to be used as medicaments.

An aspect of the invention is also a composition according to the invention for its use as a medicament, in particular in the treatment of diseases involving an mTOR enzyme with serine-threonine kinase activity in a patient.

The terms "treating" or "treatment" as used in the present invention relate to the inversion, attenuation, inhibition of progression, delay of onset, improvement and/or partial or total relief of a disease or a disorder or of one or more symptoms of the disease or of the disorder, as described hereinbelow. In certain embodiments, the treatment may be administered after one or more symptoms have developed. In certain particular embodiments, the treatment may be administered as a preventive measure, for preventing or stopping the progression of a disease or a disorder. In this context, the term "prevention" denotes a reduction of the risk of acquiring a given disease or disorder. In other embodiments, the treatment may be administered in the absence of symptoms. For example, the treatment may be administered to a predisposed individual before the appearance of the symptoms (for example in the light of a history of symptoms and/or of genetic factors or other predisposing factors). The treatment may also be continued after the disappearance of the symptoms, for example to prevent or delay their reappearance. Thus, in certain embodiments, the term "treatment" comprises the prevention of relapse or of recurrence of a disease or a disorder.

As used in the present invention, the term "patient" denotes a mammal and includes human and animal individuals, preferably a human.

The composition according to the invention is more particularly intended to be used in the treatment of dermatological complaints associated with a keratinization disorder with a proliferative, inflammatory and/or immunoallergic component.

The dermatological complaints associated with a keratinization disorder with a proliferative, inflammatory and/or immunoallergic component comprise keratinization conditions or disorders relating to cell proliferation, notably common acne, comedones, polymorphs, acne rosacea, nodulocystic acne, acne conglobata, senile acne, and secondary acnes such as solar acne, medication-related acne or occupational acne, other keratinization disorders, notably ichthyosis, ichthyosiform conditions, Darier's disease, palmoplantar keratoderma, leukoplakia and leukoplakiform conditions, and cutaneous or mucous (buccal) lichen, other dermatological complaints associated with a keratinization disorder with an inflammatory and/or immunoallergic component, notably all forms of psoriasis, whether it is cutaneous, mucous or ungual psoriasis, and even psoriatic rheumatism, or cutaneous atopy, such as atopic dermatitis (or atopic eczema) or respiratory atopy or gingival hypertrophy, all dermal or epidermal proliferations, whether benign or malignant, and whether of viral origin or otherwise, such as common warts, flat warts and verruciform epidermodysplasia, oral or florid papillomatoses, and lesions or proliferations that may be induced by ultraviolet radiation, notably in the case of actinic keratoses, and basal cell and spinal cell epithelioma.

More preferably, the composition according to the invention is intended to be used in the treatment of dermatological complaints associated with a keratinization disorder with a proliferative, inflammatory and/or immunoallergic component, such as psoriasis, atopic dermatitis, actinic keratosis or acne, even more preferably atopic dermatitis.

Particularly advantageously, the composition according to the invention is intended to be used in the treatment of the inflammatory component of atopic dermatitis, and preferably the topical treatment of the inflammatory component of atopic dermatitis.

According to another particularly advantageous embodiment of the invention, the composition is intended to be used for reinforcing the skin barrier function in a patient suffering from atopic dermatitis.

The term "inflammatory component of atopic dermatitis" means an inflammation involving the CD4+ lymphocytes, eosinophils, mastocytes and Th2 cytokines.

The term "barrier function" or "skin barrier" refers to the protective role of epidermal cells, in particular of the cornified layer, with respect to the environment (i.e. water loss, physical and/or chemical attack and infectious agents).

The barrier function may be evaluated by means of the transepidermal water loss (or TEWL) test and/or histological evaluation of the epidermal thickness. The term "transepidermal water loss" means the percentage of water passing through the keratin materials (more precisely the cornified layer) and evaporating at the surface thereof. The protocol for measuring the TEWL is detailed in the examples hereinbelow.

An aspect of the present invention is also processes for preparing the compounds of formula (I) or (Ia), in particular according to the reaction scheme given in FIG. 1.

Several examples of production of active compounds of general formula (I) or (Ia) according to the invention and inhibitory activity results will now be given, by way of illustration and with no limiting nature.

Example 1: route for synthesizing the compound 3-(2-aminobenzoxazol-5-yl)-1-((S)-1,3-dimethylbutyl)-1H-pyrazolo[3,4-d]pyrimidine-4,6-diamine (example 1) as illustrated in FIG. 1

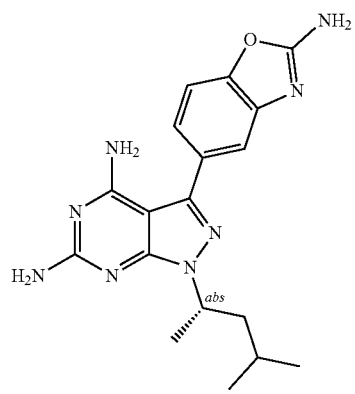 [SMILES: CC(C)C[C@H](C)n1nc(-c2ccc3oc(N)nc3c2)c2c(N)nc(N)nc21]

a) 1-((S)-1,3-dimethylbutyl)-3-iodo-1H-pyrazolo[3,4-d]pyrimidine-4,6-diamine (R)-4-Methylpentan-2-ol (0.25 ml; 2.0 mmol; 1.1 eq.) is added to 3-iodo-1H-pyrazolo[3,4-d]pyrimidine-4,6-diamine (500 mg; 1.8 mmol; 1.0 eq.) (1) and triphenylphosphine (1.43 g; 5.4 mmol; 3.0 eq.) dissolved in tetrahydrofuran (10 ml). The reaction medium is cooled to 0° C. and diisopropyl azodicarboxylate (1.1 ml; 5.4 mmol; 3.0 eq.) is then added. The reaction medium is stirred at room temperature for 30 minutes. The reaction is stopped by adding water and cold 1N sodium hydroxide solution to basic pH, and the mixture is then extracted with ethyl acetate. The organic phase is washed with saturated sodium chloride solution, dried over sodium sulfate and concentrated. The crude product is chromatographed on silica gel (25 g, solid deposition, dichloromethane/methanol eluent from 0 to 15% of methanol). 1-((S)-1,3-Dimethylbutyl)-3-iodo-1H-pyrazolo[3,4-d]pyrimidine-4,6-diamine (308 mg; 47%) (2) is obtained in the form of a pale yellow foam.

b) 3-(2-aminobenzoxazol-5-yl)-1-((S)-1,3-dimethylbutyl)-1H-pyrazolo[3,4-d]pyrimidine-4,6-diamine A solution of 1-((S)-1,3-dimethylbutyl)-3-iodo-1H-pyrazolo[3,4-d]pyrimidine-4,6-diamine (570 mg; 1.6 mmol; 1.0 eq.) (2), (2-aminobenzo[d]oxazol-5-yl)boronic acid dihydrochloride (407 mg; 1.9 mmol; 1.2 eq.) and a solution of potassium carbonate (2.4 ml; 2.0 M; 4.8 mmol; 3.0 eq.) in 1,4-dioxane (5.7 ml) is degassed under nitrogen for 10 minutes, and 1,1'-bis(diphenylphosphino)ferrocenepalladium(II) dichloride, dichloromethane (65 mg; 0.08 mmol; 0.05 eq.) is then added. The medium is heated at 110° C. for 30 minutes. The reaction is stopped by adding water and the mixture is then extracted with ethyl acetate. The organic phases are combined, washed with saturated sodium chloride solution, dried over sodium sulfate and concentrated. The crude product is chromatographed on silica gel (12 g, solid deposition, dichloromethane/methanol eluent from 0 to 15% of methanol, TLC: dichloromethane/methanol 95/5 Rf=0.07). 3-(2-Aminobenzoxazol-5-yl)-1-((S)-1,3-dimethylbutyl)-1H-pyrazolo[3,4-d]pyrimidine-4,6-diamine (399 mg; 69%) (3) is obtained in the form of a white crystalline solid after recrystallization from acetonitrile/water.

1H NMR (DMSO-d6) δ: 0.81 (d, J=6.5 Hz, 3H), 0.89 (d, J=6.5 Hz, 3H), 1.20-1.34 (m, 1H), 1.37 (d, J=6.7 Hz, 3H), 1.52 (ddd, J=13.6, 8.6, 5.1 Hz, 1H), 2.00 (ddd, J=13.6, 10.0, 5.4 Hz, 1H), 4.72-4.82 (m, 1H), 6.11 (s, 4H), 7.19 (dd, J=8.2, 1.8 Hz, 1H), 7.36 (d, J=1.9 Hz, 1H), 7.44 (dd, J=8.1, 5.2 Hz, 1H), 7.50 (s, 2H)

MS (ESI) m/z=367 [M+H]$^+$

Example 2: 3-(2-amino-6-fluorobenzoxazol-5-yl)-1-((S)-1,3-dimethylbutyl)-1H-pyrazolo[3,4-d]pyrimidine-4,6-diamine

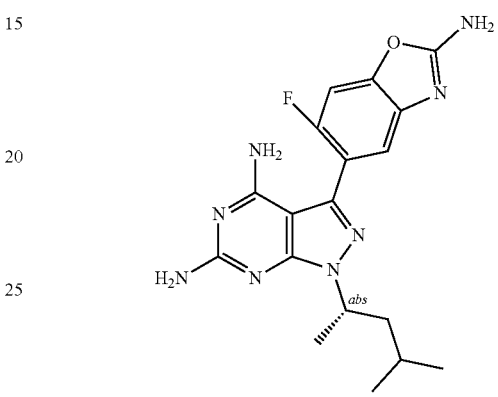

a) 1-((S)-1,3-dimethylbutyl)-3-iodo-1H-pyrazolo[3,4-d]pyrimidine-4,6-diamine (R)-4-Methylpentan-2-ol (0.25 ml; 2.0 mmol; 1.1 eq.) is added to 3-iodo-1H-pyrazolo[3,4-d]pyrimidine-4,6-diamine (500 mg; 1.8 mmol; 1.0 eq.) and triphenylphosphine (1.43 g; 5.4 mmol; 3.0 eq.) dissolved in tetrahydrofuran (10 ml). The reaction medium is cooled to 0° C. and diisopropyl azodicarboxylate (1.1 ml; 5.4 mmol; 3.0 eq.) is added. The reaction medium is stirred at room temperature for 30 minutes. The reaction is stopped by adding water and cold 1N sodium hydroxide solution to basic pH, and the mixture is then extracted with ethyl acetate. The organic phase is washed with saturated sodium chloride solution, dried over sodium sulfate and concentrated. The crude product is chromatographed on silica gel (25 g, solid deposition, dichloromethane/methanol eluent from 0 to 15% of methanol). 1-((S)-1,3-Dimethylbutyl)-3-iodo-1H-pyrazolo[3,4-d]pyrimidine-4,6-diamine (308 mg; 47%) is obtained in the form of a pale yellow foam.

b) 3-(2-amino-6-fluorobenzoxazol-5-yl)-1-((S)-1,3-dimethylbutyl)-1H-pyrazolo[3,4-d]pyrimidine-4,6-diamine A solution of 1-((S)-1,3-dimethylbutyl)-3-iodo-1H-pyrazolo[3,4-d]pyrimidine-4,6-diamine (230 mg; 0.6 mmol; 1.0 eq.), 6-fluoro-5-(4,4,5,5-tetramethyl[1,3,2]dioxaborolan-2-yl)benzoxazol-2-ylamine (213 mg; 0.8 mmol; 1.2 eq.) and a solution of potassium carbonate (0.96 ml; 2.0 M; 1.9 mmol; 3.0 eq.) in 1,4-dioxane (2.3 ml) is degassed under nitrogen for 10 minutes, and 1,1'-bis(diphenylphosphino)ferrocenepalladium(II) dichloride, dichloromethane (26 mg; 0.03 mmol; 0.05 eq.) is then added. The medium is heated at 110° C. for 2 hours. The reaction is stopped by adding water and the mixture is then extracted with ethyl acetate. The organic phases are combined and then washed with saturated sodium chloride solution, dried over sodium sulfate and evaporated. The crude product is purified by preparative HPLC (C18 column, eluent: acetonitrile in water/0.2% of ammonium carbonate).

3-(2-Amino-6-fluorobenzoxazol-5-yl)-1-((S)-1,3-dimethylbutyl)-1H-pyrazolo[3,4-d]pyrimidine-4,6-diamine (175 mg; 69%) (3) is obtained in the form of a whitish crystalline solid.

1H NMR (DMSO-d6) δ: 0.80 (d, J=6.7 Hz, 3H), 0.88 (d, J=6.5 Hz, 3H), 1.22-1.32 (m, 1H), 1.37 (d, J=6.6 Hz, 3H), 1.52 (ddd, J=13.4, 8.4, 5.0 Hz, 1H), 1.98 (ddd, J=13.6, 10.0, 5.4 Hz, 1H), 4.76 (ddd, J=9.9, 6.9, 5.3 Hz, 1H), 6.10 (s, 4H), 7.17 (d, J=6.7 Hz, 1H), 7.46 (d, J=9.2 Hz, 1H), 7.52 (s, 2H)

MS (ESI) m/z=385 [M+H]$^+$

Example 3: 3-(2-amino-4-fluorobenzoxazol-5-yl)-1-(1-methylcyclobutylmethyl)-1H-pyrazolo[3,4-d]pyrimidine-4,6-diamine

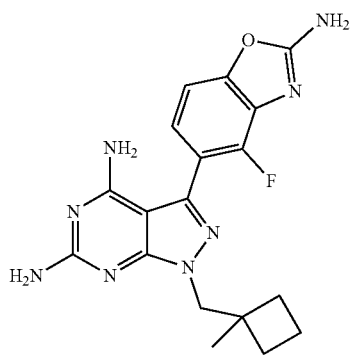 [SMILES: CC1(Cn2nc(-c3ccc4oc(N)nc4c3F)c3c(N)nc(N)nc32)CCC1]

a) Toluene-4-sulfonic acid thietan-3-ylmethyl ester p-Toluenesulfonyl chloride (782 mg; 4.1 mmol; 1.5 eq.) is added slowly at 0° C. to thietan-3-ylmethanol (300 mg; 2.7 mmol; 1.0 eq.), triethylamine (1.14 ml; 8.2 mol; 3.0 eq.) and 4-dimethylaminopyridine (33 mg; 0.3 mmol; 0.1 eq.) dissolved in dichloromethane (5.7 ml). The reaction medium is stirred at room temperature for 1 hour. The crude product is chromatographed on silica gel (25 g, liquid deposition, heptane/ethyl acetate eluent from 0 to 50% of ethyl acetate). Toluene-4-sulfonic acid thietan-3-ylmethyl ester (631 mg; 89%) is obtained in the form of a colorless oil.

b) 3-iodo-1-thietan-3-ylmethyl-1H-pyrazolo[3,4-d]pyrimidine-4,6-diamine

Toluene-4-sulfonic acid thietan-3-ylmethyl ester (618 mg; 2.4 mmol; 1.1 eq.) is added to a suspension of 3-iodo-1H-pyrazolo[3,4-d]pyrimidine-4,6-diamine (600 mg; 2.2 mmol; 1.0 eq.) and cesium carbonate (1.42 g; 4.4 mmol; 2.0 eq.) in N,N'-dimethylformamide (6.0 ml). The reaction medium is heated at 120° C. by microwave for 20 minutes. The reaction is stopped by adding water and the mixture is then extracted with ethyl acetate. The organic phases are combined, washed with saturated sodium chloride solution, dried over sodium sulfate and evaporated. The residue is taken up in ethanol and is filtered. 3-Iodo-1-thietan-3-ylmethyl-1H-pyrazolo[3,4-d]pyrimidine-4,6-diamine (412 mg; 52%) is obtained in the form of an orange-colored powder.

c) 3-(2-amino-4-fluorobenzoxazol-5-yl)-1-(1-methylcyclobutylmethyl)-1H-pyrazolo[3,4-d]pyrimidine-4,6-diamine A solution of 3-iodo-1-(1-methylcyclobutylmethyl)-1H-pyrazolo[3,4-d]pyrimidine-4,6-diamine (200 mg; 0.6 mmol; 1.0 eq.), 4-fluoro-5-(4,4,5,5-tetramethyl[1,3,2]dioxaborolan-2-yl)benzoxazol-2-ylamine (186 mg; 0.7 mmol; 1.2 eq.) and a solution of potassium carbonate (0.84 ml; 2.0 M; 1.7 mmol; 3.0 eq.) in 1,4-dioxane (2.0 ml) is degassed under nitrogen for 10 minutes, and 1,1'-bis(diphenylphosphino)ferrocenepalladium(II) dichloride, dichloromethane (23 mg; 0.03 mmol; 0.05 eq.) is then added. The medium is heated at 110° C. for 30 minutes. The reaction is stopped by adding water and the mixture is then extracted with ethyl acetate. The organic phases are combined, washed with saturated sodium chloride solution, dried over sodium sulfate and evaporated. The crude product is chromatographed on silica gel (25 g, solid deposition, dichloromethane/methanol eluent from 0 to 15% of methanol). Since the product is not pure, it is repurified by preparative HPLC (C18 column, eluent: acetonitrile in water/0.1% of formic acid). 3-(2-Amino-4-fluorobenzoxazol-5-yl)-1-(1-methylcyclobutylmethyl)-1H-pyrazolo[3,4-d]pyrimidine-4,6-diamine (81 mg; 38%) is obtained in the form of a white solid.

1H NMR (DMSO-d6) δ: 1.11 (s, 3H), 1.58-1.74 (m, 3H), 1.84 (tdd, J=7.5, 5.9, 2.1 Hz, 1H), 2.16 (qd, J=8.8, 8.0, 3.9 Hz, 2H), 4.09 (s, 2H), 6.13 (s, 2H), 7.04 (dd, J=8.2, 6.6 Hz, 1H), 7.30 (d, J=8.1 Hz, 1H), 7.68 (s, 2H)

MS (ESI) m/z=383 [M+H]$^+$

Example 4: 3-(2-amino-6-fluorobenzoxazol-5-yl)-1-(1-methylcyclobutylmethyl)-1H-pyrazolo[3,4-d]pyrimidine-4,6-diamine

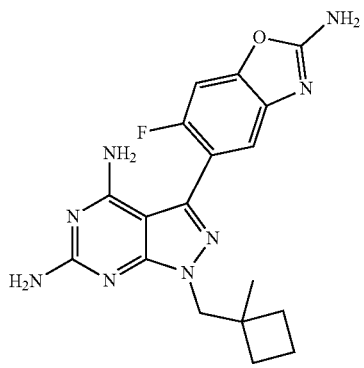 [SMILES: CC1(Cn2nc(-c3cc4nc(N)oc4cc3F)c3c(N)nc(N)nc32)CCC1]

1H NMR (DMSO-d6) δ: 1.10 (s, 3H), 1.59-1.69 (m, 3H), 1.80-1.88 (m, 1H), 4.08 (s, 2H), 6.13 (s, 4H), 7.16-7.18 (d, J=6.6 Hz, 1H), 7.46-7.48 (d, J=9.2 Hz, 1H), 7.52 (s, 2H).

MS (ESI) m/z=383 [M+H]$^+$

The compounds of examples 4-18, 20, 21, 22, 25 and 28-30 may be obtained according to the process described in FIG. 1 using precursors into which the groups $R_1$, $R_2$, $R_4$ or $R_5$ have previously been introduced (cf. FIG. 1).

Example 5: 3-(2-amino-4-fluorobenzoxazol-5-yl)-1-((S)-1,3-dimethylbutyl)-1H-pyrazolo[3,4-d]pyrimidine-4,6-diamine

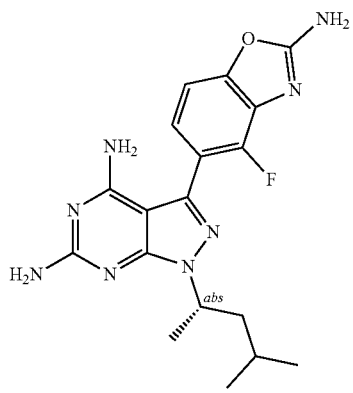 [SMILES: CC(C)C[C@H](C)n1nc(-c2ccc3oc(N)nc3c2F)c2c(N)nc(N)nc21]

a) 1-((S)-1,3-dimethylbutyl)-3-iodo-1H-pyrazolo[3,4-d]pyrimidine-4,6-diamine (R)-4-Methylpentan-2-ol (0.25 ml; 2.0 mmol; 1.1 eq.) is added to 3-iodo-1H-pyrazolo[3,4-d]pyrimidine-4,6-diamine (500 mg; 1.8 mmol; 1.0 eq.) and triphenylphosphine (1.43 g; 5.4 mmol; 3.0 eq.) dissolved in tetrahydrofuran (10 ml). The reaction medium is cooled to 0° C. and diisopropyl azodicarboxylate (1.1 ml; 5.4 mmol; 3.0 eq.) is then added. The reaction medium is stirred at room temperature for 30 minutes. The reaction is stopped by adding water and cold 1N sodium hydroxide solution to basic pH, and the mixture is then extracted with ethyl acetate. The organic phase is washed with saturated sodium chloride solution, dried over sodium sulfate and concentrated. The crude product is chromatographed on silica gel (25 g, solid deposition, dichloromethane/methanol eluent from 0 to 15% of methanol). 1-((S)-1,3-Dimethylbutyl)-3-iodo-1H-pyrazolo[3,4-d]pyrimidine-4,6-diamine (308 mg; 47%) is obtained in the form of a pale yellow foam.

b) 3-(2-Amino-4-fluorobenzoxazol-5-yl)-1-((S)-1,3-dimethylbutyl)-1H-pyrazolo[3,4-d]pyrimidine-4,6-diamine A solution of 1-((S)-1,3-dimethylbutyl)-3-iodo-1H-pyrazolo[3,4-d]pyrimidine-4,6-diamine (160 mg; 0.4 mmol; 1.0 eq.), 4-fluoro-5-(4,4,5,5-tetramethyl[1,3,2]dioxaborolan-2-yl)benzoxazol-2-ylamine (148 mg; 0.5 mmol; 1.2 eq.) and a solution of potassium carbonate (0.67 ml; 2.0 M; 1.3 mmol; 3.0 eq.) in 1,4-dioxane (1.6 ml) is degassed under nitrogen for 10 minutes, and 1,1'-bis(diphenylphosphino)ferrocenepalladium(II) dichloride, dichloromethane (18 mg; 0.02 mmol; 0.05 eq.) is then added. The medium is heated at 110° C. for 30 minutes. The reaction is stopped by adding water and the mixture is then extracted with ethyl acetate. The organic phases are combined, washed with saturated sodium chloride solution, dried over sodium sulfate and evaporated. The crude product is chromatographed on silica gel (25 g, solid deposition, dichloromethane/methanol eluent from 0 to 15% of methanol). 3-(2-Amino-4-fluorobenzoxazol-5-yl)-1-((S)-1,3-dimethylbutyl)-1H-pyrazolo[3,4-d]pyrimidine-4,6-diamine (75 mg; 44%) (3) is obtained in the form of a beige-colored crystalline solid after recrystallization from acetonitrile/water.

1H NMR (DMSO-d6) δ: 0.80 (d, J=6.5 Hz, 3H), 0.88 (d, J=6.5 Hz, 3H), 1.28 (dt, J=14.4, 6.8 Hz, 1H), 1.37 (d, J=6.7 Hz, 3H), 1.52 (ddd, J=13.4, 8.5, 5.0 Hz, 1H), 1.98 (ddd, J=14.2, 9.9, 5.3 Hz, 1H), 4.77 (dt, J=10.8, 5.9 Hz, 1H), 6.10 (s, 4H), 6.98-7.11 (m, 1H), 7.30 (d, J=8.3 Hz, 1H), 7.67 (s, 2H)
MS (ESI) m/z=325 [M+H]+

Example 6: N-(5-(4,6-diamino-1-(2,2-dimethylbutyl)-1H-pyrazolo[3,4-d]pyrimidin-3-yl)benzo[d]oxazol-2-yl)acetamide

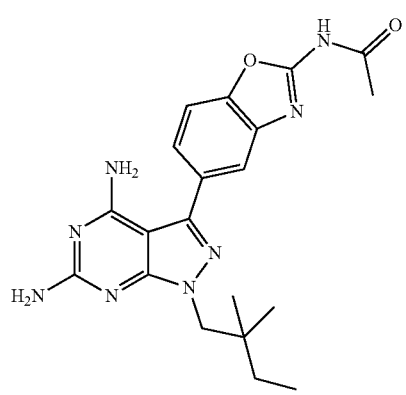 [SMILES: CCC(C)(C)Cn1nc(-c2ccc3oc(NC(C)=O)nc3c2)c2c(N)nc(N)nc21]

1H NMR (DMSO-d6) δ: 0.89 (t, J=7.5 Hz, 3H), 0.91 (s, 6H), 1.33 (q, J=7.5 Hz, 2H), 2.23 (s, 3H), 3.95 (s, 2H), 6.12-6.36 (brs, 4H), 7.48 (dd, J=8.4, 1.8 Hz, 1H), 7.68-7.74 (m, 2H), 11.70 (br s, 1H)
MS (ESI) m/z=409 [M+H]+

Example 7: 3-(2-aminobenzoxazol-5-yl)-1-(2,2-dimethylpropyl)-1H-pyrazolo[3,4-d]pyrimidine-4,6-diamine

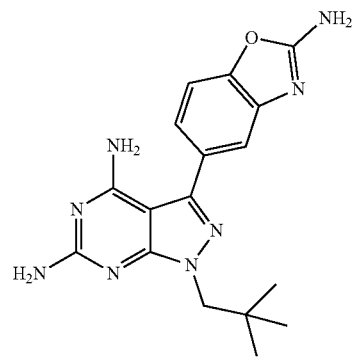 [SMILES: CC(C)(C)Cn1nc(-c2ccc3oc(N)nc3c2)c2c(N)nc(N)nc21]

a) 1-(2,2-dimethylpropyl)-3-iodo-1H-pyrazolo[3,4-d]pyrimidine-4,6-diamine

Cesium carbonate (2.36 g; 7.3 mmol; 2.0 eq.) and then 1-bromo-2,2-dimethylpropane (502 μl; 4.0 mmol; 1.1 eq.) are added to a solution of 3-iodo-1H-pyrazolo[3,4-d]pyrimidine-4,6-diamine (1.00 g; 3.6 mmol; 1.0 eq.) in N,N'-dimethylformamide (20 ml). The reaction medium is heated at 110° C. for 2 days. The cooled reaction medium is hydrolyzed with water and extracted with ethyl acetate. The organic phases are combined, washed with water, dried over magnesium sulfate, filtered and evaporated. The residue is chromatographed on silica gel eluted with dichloromethane/methanol (98/2 to 95/5). 1-(2,2-Dimethylpropyl)-3-iodo-1H-pyrazolo[3,4-d]pyrimidine-4,6-diamine (1.04 g; 83%) is obtained in the form of a white solid.

b) 3-(2-aminobenzoxazol-5-yl)-1-(2,2-dimethylpropyl)-1H-pyrazolo[3,4-d]pyrimidine-4,6-diamine A solution of 1-(2,2-dimethylpropyl)-3-iodo-1H-pyrazolo[3,4-d]pyrimidine-4,6-diamine (323 mg; 0.9 mmol; 1.0 eq.), 5-(4,4,5,5-tetramethyl-1,3,2-dioxaborolan-2-yl)benzo[d]oxazol-2-amine (364 mg; 1.4 mmol; 1.5 eq.) and a solution of potassium carbonate (1.4 ml; 2.0 M; 2.8 mmol; 3.0 eq.) in 1,4-dioxane (3.2 ml) is degassed under nitrogen for 10 minutes, and 1,1'-bis(diphenylphosphino)ferrocenepalladium(II) dichloride, dichloromethane (152 mg; 0.19 mmol; 0.20 eq.) is then added. The medium is heated at 110° C. for 30 minutes. The aqueous phase is removed and the medium is filtered through Celite. The solvent is evaporated off and the residue is chromatographed on silica gel eluted with dichloromethane/methanol (95/5 to 80/20). The solvent is concentrated and the insoluble material is filtered off and dried under vacuum at 40° C. 3-(2-Aminobenzoxazol-5-yl)-1-(2,2-dimethylpropyl)-1H-pyrazolo[3,4-d]pyrimidine-4,6-diamine (160 mg; 48%) is obtained in the form of a salmon-beige solid. 1H NMR (DMSO-d6) δ: 0.97 (s, 9H), 3.93 (s, 2H), 6.12 (s, 4H), 7.19-7.21 (dd, J=8.1, 1.7 Hz, 1H), 7.37 (d, J=1.5 Hz, 1H), 7.42-7.44 (d, J=8.1 Hz, 1H), 7.49 (s, 2H).

MS (ESI) m/z=353 [M+H]$^+$

Example 8: 3-(2-aminobenzoxazol-5-yl)-1-(2,2-dimethylbutyl)-1H-pyrazolo[3,4-d]pyrimidine-4,6-diamine

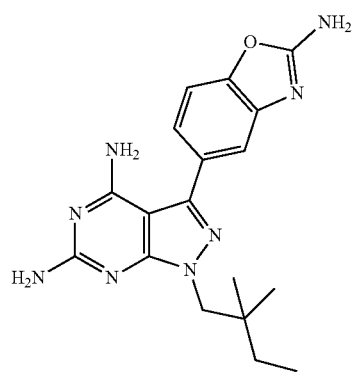 [SMILES: CCC(C)(C)Cn1nc(-c2ccc3oc(N)nc3c2)c2c(N)nc(N)nc21]

a) 1-(2,2-dimethylbutyl)-3-iodo-1H-pyrazolo[3,4-d]pyrimidine-4,6-diamine

Di-tert-butyl azodicarboxylate (1.25 g; 5.4 mmol; 1.5 eq.) is added to a solution, cooled to 0° C., of triphenylphosphine (1.43 g; 5.4 mmol; 1.5 eq.) in toluene (10 ml). The reaction medium is stirred at 0° C. for 30 minutes. 2,2-Dimethylbutan-1-ol (555 mg; 5.4 mmol; 1.5 eq.) is then added dropwise and the reaction medium is stirred at 0° C. for 30 minutes. Finally, 3-iodo-1H-pyrazolo[3,4-d]pyrimidine-4,6-diamine (1.00 g; 3.6 mmol; 1.0 eq.) is added and the reaction medium is heated at 110° C. for 1 hour 15 minutes.

This step is repeated, but with di-tert-butyl azodicarboxylate (0.42 g; 1.8 mmol; 0.5 eq.), triphenylphosphine (0.48 g; 1.8 mmol; 0.5 eq.) and 2,2-dimethylbutan-1-ol (185 mg; 1.8 mmol; 0.5 eq.) in 3.5 ml of toluene. This solution is added to the reaction medium, which is heated at 110° C. for 1 hour 10 minutes.

The reaction medium is concentrated under vacuum. The residue is taken up with a solution of acetic acid (8 ml) and water (2 ml). The reaction medium is heated at 100° C. for 1 hour 30 minutes. The reaction medium is evaporated under nitrogen and the residue is chromatographed on silica gel eluted with dichloromethane/methanol (98/2 to 95/5). 1-(2,2-Dimethylbutyl)-3-iodo-1H-pyrazolo[3,4-d]pyrimidine-4,6-diamine (0.81 g; 62%) is obtained in the form of a yellow solid.

b) 3-(2-aminobenzoxazol-5-yl)-1-(2,2-dimethylbutyl)-1H-pyrazolo[3,4-d]pyrimidine-4,6-diamine A solution of 1-(2,2-dimethylbutyl)-3-iodo-1H-pyrazolo[3,4-d]pyrimidine-4,6-diamine (880 mg; 2.4 mmol; 1.0 eq.), 5-(4,4,5,5-tetramethyl-1,3,2-dioxaborolan-2-yl)benzo[d]oxazol-2-amine (953 mg; 3.7 mmol; 1.5 eq.) and a solution of potassium carbonate (3.7 ml; 2.0 M; 7.3 mmol; 3.0 eq.) in 1,4-dioxane (8.8 ml) is degassed under nitrogen for 10 minutes, and 1,1'-bis(diphenylphosphino)ferrocenepalladium(II) dichloride, dichloromethane (399 mg; 0.5 mmol; 0.20 eq.) is then added. The reaction medium is heated at 110° C. for 45 minutes. The aqueous phase is removed and the medium is filtered through Celite. The residue is purified by preparative HPLC under acidic conditions (25% to 35% ACN). The acetonitrile is evaporated off and the aqueous phase is neutralized with saturated sodium hydrogen carbonate solution and extracted with ethyl acetate. The organic phases are combined, washed with water, dried over magnesium sulfate, filtered and concentrated. The solid is filtered off and dried under vacuum at 40° C. 3-(2-Aminobenzoxazol-5-yl)-1-(2,2-dimethylbutyl)-1H-pyrazolo[3,4-d]pyrimidine-4,6-diamine (414 mg; 46%) is obtained in the form of a pale beige solid.

1H NMR (DMSO-d6) δ: 0.87-0.91 (t, J=7.6 Hz, 3H), 0.91 (s, 6H), 1.30-1.35 (q, J=7.6 Hz, 2H), 3.94 (s, 2H), 6.10 (s, 4H), 7.19-7.21 (dd, J=8.1, 1.7 Hz, 1H), 7.36 (d, J=1.6 Hz, 1H), 7.42-7.44 (d, J=8.1 Hz, 1H), 7.49 (s, 2H).

MS (ESI) m/z=367 [M+H]$^+$

Example 9: 3-(2-aminobenzoxazol-5-yl)-1-(3-methylthietan-3-ylmethyl)-1H-pyrazolo[3,4-d]pyrimidine-4,6-diamine

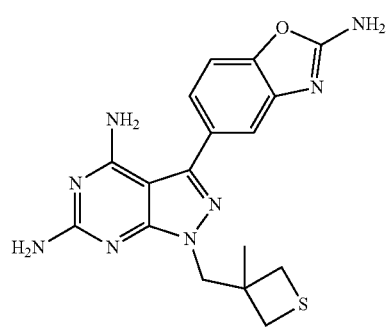 [SMILES: CC1(Cn2nc(-c3ccc4oc(N)nc4c3)c3c(N)nc(N)nc32)CSC1]

1H NMR (DMSO-d6) δ: 1.29 (s, 3H), 2.79-2.81 (d, J=9.2 Hz, 2H), 3.43-3.46 (d, J=9.4 Hz, 2H), 4.22 (s, 2H), 6.19 (s, 4H), 7.20-7.22 (d, J=8.0 Hz, 1H), 7.37 (s, 1H), 7.43-7.45 (d, J=8.1 Hz, 1H), 7.50 (s, 2H).

MS (ESI) m/z=383 [M+H]$^+$

Example 10: 1-(2,2-dimethylbutyl)-3-iodo-1H-pyrazolo[3,4-d]pyrimidine-4,6-diamine

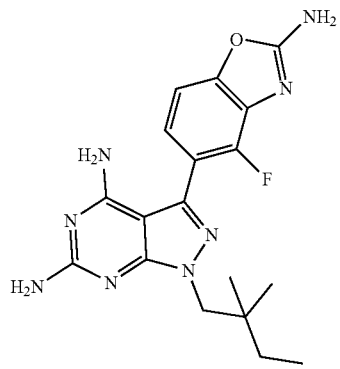 [SMILES: CCC(C)(C)Cn1nc(-c2ccc3oc(N)nc3c2F)c2c(N)nc(N)nc21]

1H NMR (DMSO-d6) δ: 0.89 (m, 9H), 1.32 (q, J=7.4 Hz, 2H), 3.95 (s, 2H), 6.10 (s, 3H), 7.04 (dd, J=8.2, 6.6 Hz, 1H), 7.30 (d, J=8.2 Hz, 1H), 7.68 (s, 2H).
MS (ESI) m/z=385 [M+H]+

Example 11: 1-(2,2-dimethylpropyl)-3-(2-ethylaminobenzoxazol-5-yl)-1H-pyrazolo[3,4-d]pyrimidine-4,6-diamine

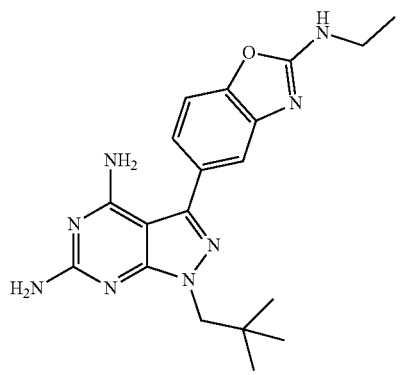 [SMILES: CCNc1nc2cc(-c3nn(CC(C)(C)C)c4nc(N)nc(N)c34)ccc2o1]

1H NMR (DMSO-d6) δ: 0.97 (s, 9H), 1.20 (t, J=7.2 Hz, 3H), 3.36 (qd, J=7.2, 5.7 Hz, 2H), 3.93 (s, 2H), 6.11 (brs, 4H), 7.20 (dd, J=8.1, 1.8 Hz, 1H), 7.39 (dd, J=1.8, 0.4 Hz, 1H), 7.44 (dd, J=8.1, 0.4 Hz, 1H), 8.00 (t, J=5.7 Hz, 1H).
MS (ESI) m/z=381 [M+H]+

Example 12: 3-(2-aminobenzoxazol-5-yl)-1-(2,2-dimethylbut-3-enyl)-1H-pyrazolo[3,4-d]pyrimidine-4,6-diamine

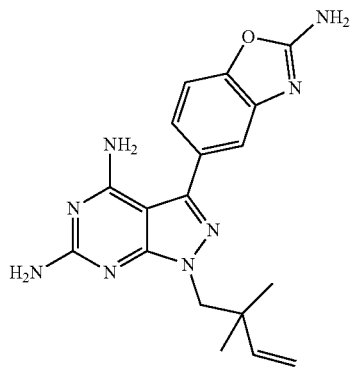 [SMILES: C=CC(C)(C)Cn1nc(-c2ccc3oc(N)nc3c2)c2c(N)nc(N)nc21]

1H NMR (DMSO-d6) δ: 1.08 (s, 6H), 4.03 (s, 2H), 4.86-5.09 (m, 2H), 6.00 (dd, J=17.5, 10.8 Hz, 1H), 6.13 (s, 3H), 7.20 (dd, J=8.1, 1.7 Hz, 1H), 7.36 (d, J=1.7 Hz, 1H), 7.44 (d, J=8.2 Hz, 1H), 7.50 (s, 2H)
MS (ESI) m/z=365 [M+H]+

Example 13: (+)-3-(2-aminobenzoxazol-5-yl)-1-((S)-2-methyl-2-tetrahydrofuran-2-ylpropyl)-1H-pyrazolo[3,4-d]pyrimidine-4,6-diamine

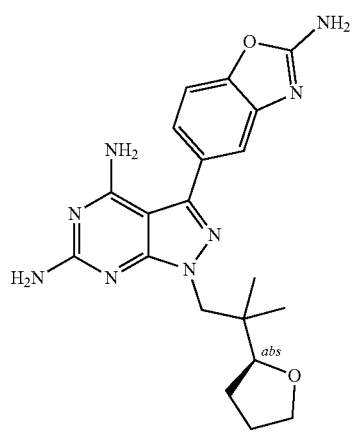 [SMILES: CC(C)(Cn1nc(-c2ccc3oc(N)nc3c2)c2c(N)nc(N)nc21)[C@@H]1CCCO1]

1H NMR (DMSO-d6) δ: 0.88-0.89 (d, J=1.7 Hz, 6H), 1.63-1.70 (m, 1H), 1.78-1.91 (m, 3H), 3.63-3.72 (m, 2H), 3.74-3.79 (m, 1H), 3.97-4.00 (d, J=13.8 Hz, 1H), 4.12-4.15 (d, J=13.8 Hz, 1H), 6.15 (s, 4H), 7.19-7.21 (dd, J=8.1, 1.7 Hz, 1H), 7.36-7.37 (d, J=1.2 Hz, 1H), 7.43-7.45 (d, J=8.1 Hz, 1H), 7.52 (s, 2H).
MS (ESI) m/z=409 [M+H]+

Example 14: 3-(2-aminobenzoxazol-5-yl)-1-(2,2-dimethylbut-3-ynyl)-1H-pyrazolo[3,4-d]pyrimidine-4,6-diamine

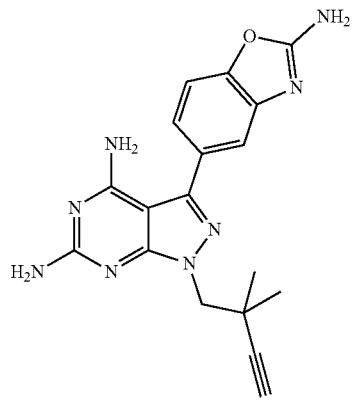 [SMILES: C#CC(C)(C)Cn1nc(-c2ccc3oc(N)nc3c2)c2c(N)nc(N)nc21]

1H NMR (DMSO-d6) δ: 1.26 (s, 6H), 2.99 (s, 1H), 4.18 (s, 2H), 5.96-6.47 (m, 4H), 7.21 (dd, J=8.1, 1.7 Hz, 1H), 7.37 (d, J=1.7 Hz, 1H), 7.44 (d, J=8.1 Hz, 1H), 7.51 (s, 2H)
MS (ESI) m/z=363 [M+H]+

Example 15: 3-[4,6-diamino-3-(2-aminobenzoxazol-5-yl)pyrazolo[3,4-d]pyrimidin-1-yl]-2,2-dimethyl-propan-1-ol

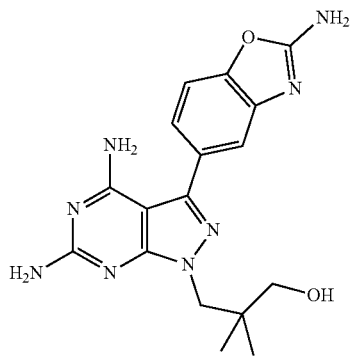 [SMILES: CC(C)(CO)Cn1nc(-c2ccc3oc(N)nc3c2)c2c(N)nc(N)nc21]

1H NMR (DMSO-d6) δ: 0.89 (s, 6H), 3.10 (d, J=6.2 Hz, 2H), 5.08 (t, J=6.6 Hz, 1H), 6.27 (s, 4H), 7.20 (dd, J=8.0, 1.8 Hz, 1H), 7.36 (d, J=1.8 Hz, 1H), 7.44 (d, J=8.0 Hz, 1H), 7.50 (s, 2H)
MS (ESI) m/z=369 [M+H]+

Example 16: 3-(2-aminobenzoxazol-5-yl)-1-(2-methyl-2-methylsulfanylpropyl)-1H-pyrazolo[3,4-d]pyrimidine-4,6-diamine

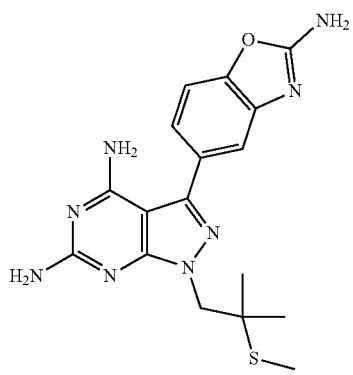 [SMILES: CSC(C)(C)Cn1nc(-c2ccc3oc(N)nc3c2)c2c(N)nc(N)nc21]

1H NMR (DMSO-d6) δ: 1.74 (s, 6H), 1.85 (s, 3H), 3.35 (s, 2H), 6.06 (s, 4H), 7.16-7.18 (dd, J=8.1, 1.4 Hz, 1H), 7.34 (d, J=1.2 Hz, 1H), 7.42-7.44 (d, J=8.1 Hz, 1H), 7.49 (s, 2H).
MS (ESI) m/z=385 [M+H]+

Example 17: 3-(2-amino-4-chlorobenzoxazol-5-yl)-1-(2,2-dimethylpropyl)-1H-pyrazolo[3,4-d]pyrimidine-4,6-diamine

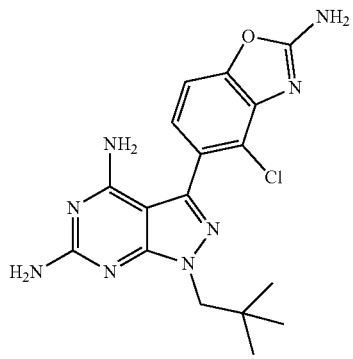 [SMILES: CC(C)(C)Cn1nc(-c2ccc3oc(N)nc3c2Cl)c2c(N)nc(N)nc21]

1H NMR (DMSO-d6) δ: 0.97 (s, 9H), 3.94 (s, 2H), 6.10 (s, 4H), 7.02-7.04 (d, J=7.9 Hz, 1H), 7.39-7.41 (d, J=8.1 Hz, 1H), 7.77 (s, 2H).
MS (ESI) m/z=387 [M+H]+

Example 18: 3-(2-amino-6-methoxybenzoxazol-5-yl)-1-(2,2-dimethylpropyl)-1H-pyrazolo[3,4-d]pyrimidine-4,6-diamine

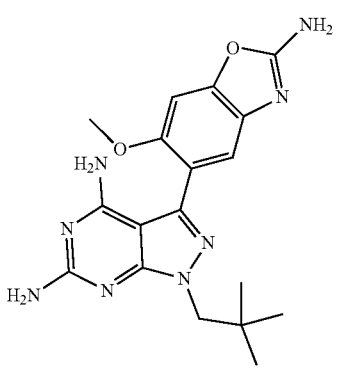 [SMILES: COc1cc2oc(N)nc2cc1-c1nn(CC(C)(C)C)c2nc(N)nc(N)c12]

1H NMR (DMSO-d6) δ: 0.97 (s, 9H), 3.76 (s, 3H), 3.91 (s, 2H); 6.03 (s, 2H), 7.09 (s, 1H), 7.29 (d, J=3.0 Hz, 3H)
MS (ESI) m/z=383 [M+H]+

Figure 3:
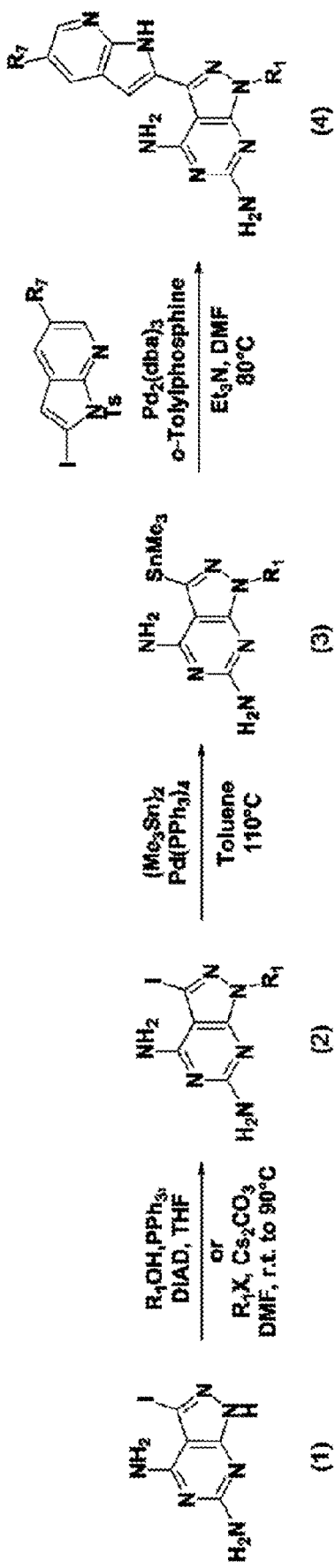
FIG. 3 represents a route for synthesizing the compound 2-[4,6-diamino-1-(2,2-dimethylpropyl)-1H-pyrazolo[3,4-d]pyrimidin-3-yl]-1H-pyrrolo[2,3-b]pyridin-5-ol (example 19)

Example 19: 2-[4,6-diamino-1-(2,2-dimethylpropyl)-1H-pyrazolo[3,4-d]pyrimidin-3-yl]-1H-pyrrolo[2,3-b]pyridin-5-ol This compound may be obtained according to the process presented in FIG. 3.

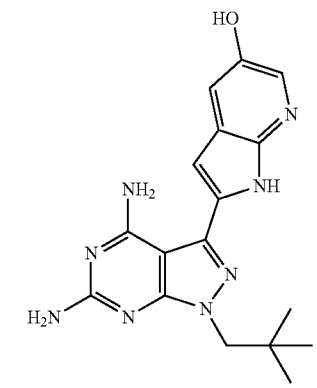 [SMILES: CC(C)(C)Cn1nc(-c2cc3cc(O)cnc3[nH]2)c2c(N)nc(N)nc21]

a) 1-Neopentyl-3-(trimethylstannyl)-1H-pyrazolo[3,4-d]pyrimidine-4,6-diamine

To a solution of 1-(2,2-dimethylpropyl)-3-iodopyrazolo[3,4-d]pyrimidine-4,6-diamine (1.37 g; 3.97 mmol; 1 eq.) in toluene (0.15 M), degassed with argon, is added hexamethyldistannane (1.56 g, 4.75 mmol; 1.2 eq.) followed by tetrakis(triphenylphosphine)palladium (0) (0.2 mmol; 0.05 eq.). The mixture is stirred at 110° C. for 30 minutes. The mixture is directly concentrated under vacuum and the residue is purified on basic alumina gel to give 1-neopentyl-3-(trimethylstannyl)-1H-pyrazolo[3,4-d]pyrimidine-4,6-diamine (792 mg; 2.06 mmol; 52%) in the form of a brown solid.

b) 3-(5-Methoxy-1-(phenylsulfonyl)-1H-pyrrolo[2,3-b]pyridin-2-yl)-1-neopentyl-1H-pyrazolo[3,4-d]pyrimidine-4,6-diamine To a solution of 3-trimethylstannylpyrazolo[3,4-d]pyrimidine-4,6-diamine (1 eq.) in N,N'-dimethylformamide (0.14 M), degassed with argon, is added 2-iodo-5-methoxy-1-(phenylsulfonyl)-1H-pyrrolo[2,3-b]pyridine (1.6 mmol, 1 eq.) followed by tris(dibenzylideneacetone)dipalladium (0) (0.16 mmol; 0.1 eq), tri-o-tolylphosphine (0.48 mmol; 0.3 eq.) and triethylamine (0.48 mmol; 3 eq.). The mixture is then stirred at 80° C. for 2 hours to obtain total conversion. After returning to room temperature, the mixture is diluted by adding water and the aqueous phase is then extracted with ethyl acetate. The organic phases are combined, washed with saturated sodium chloride solution, dried over sodium sulfate and concentrated. The crude product is chromatographed on silica gel. 3-(5-Methoxy-1-(phenylsulfonyl)-1H-pyrrolo[2,3-b]pyridin-2-yl)-1-neopentyl-1H-pyrazolo[3,4-d]pyrimidine-4,6-diamine (234 mg; 29%) is obtained in the form of a colorless solid.

c) 2-[4,6-Diamino-1-(2,2-dimethylpropyl)-1H-pyrazolo[3,4-d]pyrimidin-3-yl]-1H-pyrrolo[2,3-b]pyridin-5-ol To a solution of 3-(5-methoxy-1-(phenylsulfonyl)-1H-pyrrolo[2,3-b]pyridin-2-yl)-1-neopentyl-1H-pyrazolo[3,4-d]pyrimidine-4,6-diamine (1 eq.) in methanol (0.5 M) is added potassium carbonate (2 eq.). The mixture is stirred at 65° C. until conversion is complete, and is diluted with a 1/1 water/ethyl acetate mixture. The aqueous phase is extracted with ethyl acetate and the organic phases are combined, washed with saturated sodium chloride solution, dried over sodium sulfate and concentrated. The product is used directly in the next step without further purification.

To a solution of 3-(5-methoxy-1H-pyrrolo[2,3-b]pyridin-2-yl)-1-neopentyl-1H-pyrazolo[3,4-d]pyrimidine-4,6-diamine (1 eq.) in dichloromethane (0.06 M) at −78° C. is added a solution of boron tribromide (1 M in dichloromethane; 9 eq.). The reaction mixture is stirred for 14 hours with gradual return to room temperature, the reaction is stopped by adding saturated sodium bicarbonate solution at 0° C., and the aqueous phase is then extracted with ethyl acetate. The organic phases are combined, washed with saturated sodium chloride solution, dried over sodium sulfate and concentrated. The crude product is chromatographed on silica gel. 2-[4,6-Diamino-1-(2,2-dimethylpropyl)-1H-pyrazolo[3,4-d]pyrimidin-3-yl]-1H-pyrrolo[2,3-b]pyridin-5-ol (16.5 mg; 44%) is obtained in the form of a colorless solid.

1H NMR (DMSO-d6) δ: 0.98 (s, 9H), 3.96 (s, 2H), 6.18 (s, 2H), 6.45 (s, 2H), 6.58 (s, 1H), 7.33 (d, J=2.61 Hz, 1H), 7.88 (d, J=2.61 Hz, 1H), 9.15 (s, 1H), 11.70 (s, 1H).

MS (ESI) m/z=353 [M+H]+

Example 20: 3-(2-amino-6-methoxybenzoxazol-5-yl)-1-(2,2-dimethylbutyl)-1H-pyrazolo[3,4-d]pyrimidine-4,6-diamine

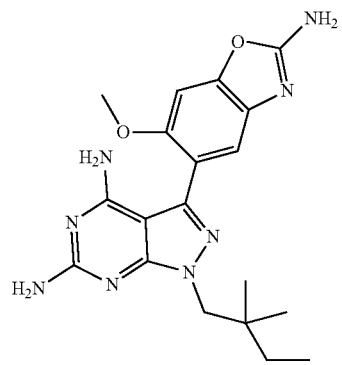 [SMILES: CCC(C)(C)Cn1nc(-c2cc3nc(N)oc3cc2OC)c2c(N)nc(N)nc21]

1H NMR (DMSO-d6) δ: 0.90 (s, 9H), 1.31-1.33 (d, J=6.2 Hz, 2H), 3.75 (s, 3H), 3.91 (s, 2H), 6.03 (s, 4H), 7.07 (s, 1H), 7.28 (s, 1H), 7.30 (s, 2H).

MS (ESI) m/z=397 [M+H]+

Example 21: 3-(2-aminobenzoxazol-5-yl)-1-isopropyl-1H-pyrazolo[3,4-d]pyrimidine-4,6-diamine

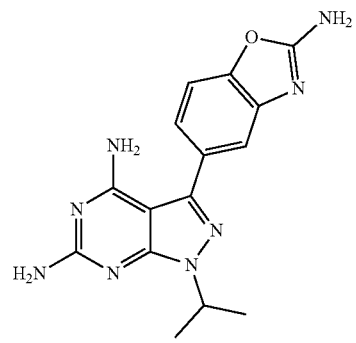 [SMILES: CC(C)n1nc(-c2ccc3oc(N)nc3c2)c2c(N)nc(N)nc21]

1H NMR (DMSO-d6) δ: 1.43 (d, J=6.7 Hz, 6H), 4.79-4.85 (p, J=6.7 Hz, 1H), 6.14 (s, 2H), 7.18-7.21 (dd, J=8.1-1.7 Hz, 1H), 7.36 (d, J=1.7 Hz, 1H), 7.43 (d, J=8.1 Hz, 1H), 7.50 (s, 2H).

MS (ESI) m/z=325 [M+H]+

Example 22: 3-(2-aminobenzoxazol-5-yl)-1-(2-ethyl-2-methanesulfonylbutyl)-1H-pyrazolo[3,4-d]pyrimidine-4,6-diamine

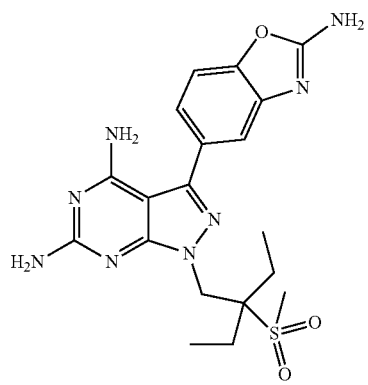 [SMILES: CCC(CC)(Cn1nc(-c2ccc3oc(N)nc3c2)c2c(N)nc(N)nc21)S(C)(=O)=O]

1H NMR (DMSO-d6) δ: 1.02 (t, J=7.4 Hz, 6H), 1.90 (p, J=7.3 Hz, 4H), 3.09 (s, 3H), 4.54 (s, 2H), 6.23 (s, 2H), 7.20 (dd, J=8.1, 1.7 Hz, 1H), 7.37 (d, J=1.7 Hz, 1H), 7.45 (d, J=8.1 Hz, 1H), 7.51 (s, 2H)

MS (ESI) m/z=445 [M+H]+

Figure 4:
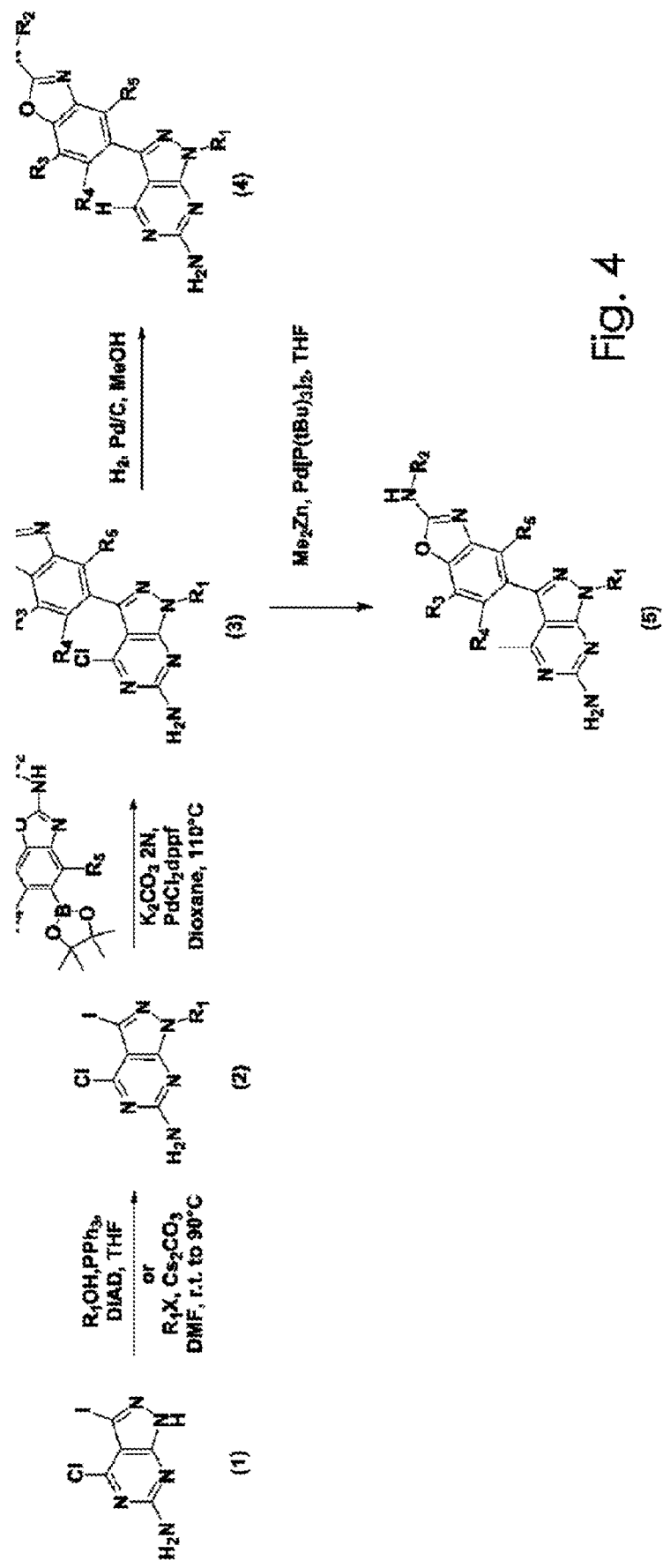
FIG. 4 represents a route for synthesizing the compounds 3-(2-aminobenzoxazol-5-yl)-4-chloro-1-isobutyl-1H-pyrazolo[3,4-d]pyrimidin-6-ylamine (example 23), 3-(2-aminobenzoxazol-5-yl)-1-isopropyl-1H-pyrazolo[3,4-d]pyrimidin-6-ylamine (example 24) and 5-(6-amino-4-methyl-1-neopentyl-1H-pyrazolo[3,4-d]pyrimidin-3-yl)benzo[d]oxazol-2-amine (example 27)

Example 23: 3-(2-aminobenzoxazol-5-yl)-4-chloro-1-isobutyl-1H-pyrazolo[3,4-d]pyrimidin-6-ylamine This compound may be obtained according to the process presented in FIG. 4.

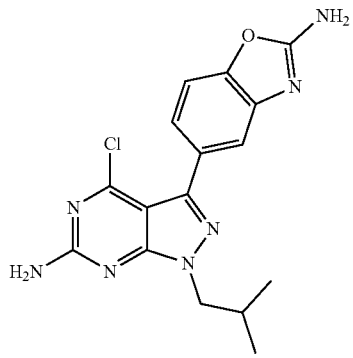 [SMILES: CC(C)Cn1nc(-c2ccc3oc(N)nc3c2)c2c(Cl)nc(N)nc21]

1H NMR (DMSO-d6) δ: 0.89 (d, J=6.8 Hz, 6H), 2.19-2.32 (m, 1H), 4.03 (d, J=7.3 Hz, 2H), 7.24-7.30 (m, 3H), 7.40 (d, J=8.2 Hz, 1H), 7.42-7.50 (m, 3H).

MS (ESI) m/z=358 [M+H]+

Example 24: 3-(2-aminobenzoxazol-5-yl)-1-isopropyl-1H-pyrazolo[3,4-d]pyrimidin-6-ylamine This compound may be obtained according to the process presented in FIG. 4.

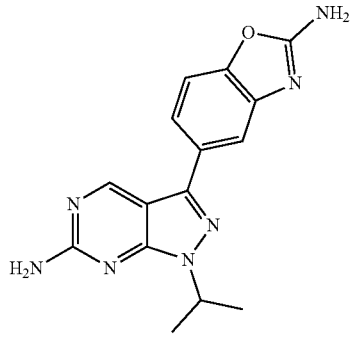 [SMILES: CC(C)n1nc(-c2ccc3oc(N)nc3c2)c2cnc(N)nc21]

1H NMR (DMSO-d6) δ: 1H NMR (400 MHz, DMSO-d6) δ 1.48 (d, J=6.7 Hz, 6H), 4.90 (p, J=6.6 Hz, 1H), 6.90 (s, 2H), 7.41 (d, J=8.1 Hz, 1H), 7.50 (s, 2H), 7.59 (dd, J=8.2, 1.7 Hz, 1H), 7.72 (d, J=1.7 Hz, 1H), 9.06 (s, 1H).

MS (ESI) m/z=310 [M+H]+

Example 25: 3-(2-amino-6-chlorobenzoxazol-5-yl)-1-((S)-1,2-dimethylpropyl)-1H-pyrazolo[3,4-d]pyrimidine-4,6-diamine

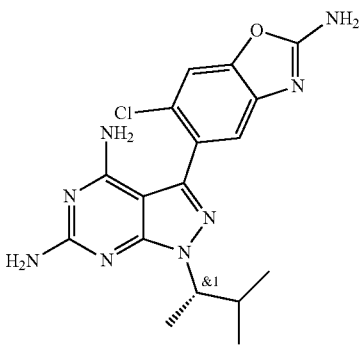 [SMILES: CC(C)[C@H](C)n1nc(-c2cc3nc(N)oc3cc2Cl)c2c(N)nc(N)nc21]

1H NMR (DMSO-d6) δ: 0.69 (d, J=6.7 Hz, 3H), 0.97 (d, J=6.7 Hz, 3H), 1.41 (d, J=6.8 Hz, 3H), 2.13 (dt, J=8.8, 6.6 Hz, 1H), 4.28-4.40 (m, 1H), 6.09 (s, 2H), 7.18 (s, 1H), 7.63 (s, 1H), 7.65 (s, 2H)

MS (ESI) m/z=387 [M+H]+

Figure 2:
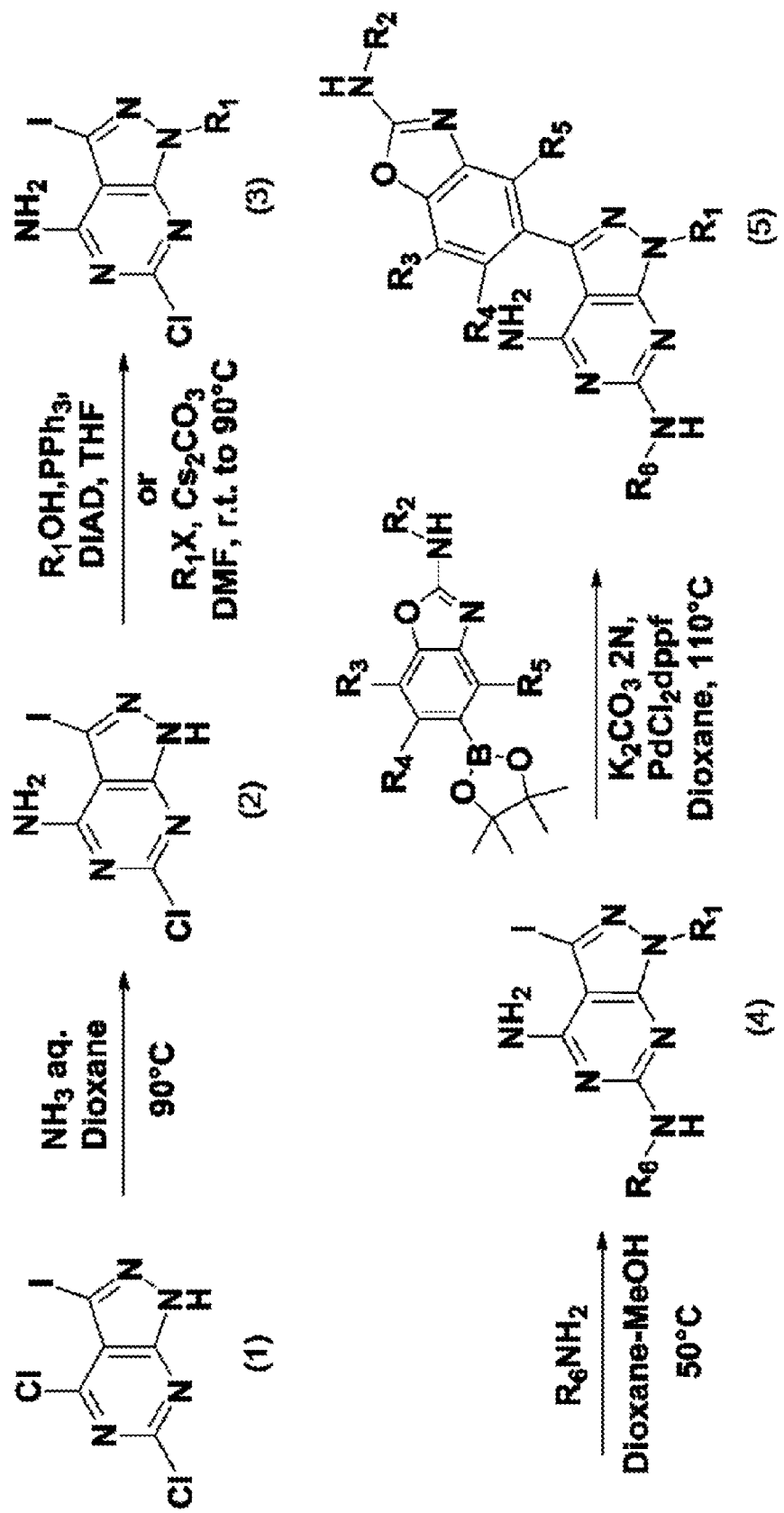
FIG. 2 represents a route for synthesizing the compound 3-(2-aminobenzoxazol-5-yl)-1-isopropyl-N⁶-methyl-1H-pyrazolo[3,4-d]pyrimidine-4,6-diamine (example 26)

Example 26: 3-(2-Aminobenzoxazol-5-yl)-1-isopropyl-N6-methyl-1H-pyrazolo[3,4-d]pyrimidine-4,6-diamine This compound may be obtained according to the process presented in FIG. 2.

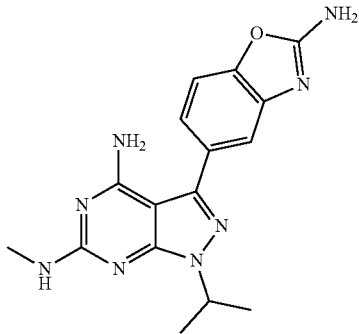 [SMILES: CNc1nc(N)c2c(-c3ccc4oc(N)nc4c3)nn(C(C)C)c2n1]

a) 6-Chloro-3-iodo-1H-pyrazolo[3,4-d]pyrimidin-4-ylamine 4,6-Dichloro-3-iodo-1H-pyrazolo[3,4-d]pyrimidine (15.8 g; 50.2 mmol; 1 eq.) (1) is dissolved in 1,4-dioxane (480 mL; 0.1 M). Aqueous ammonia solution (474.00 ml; 32.00% g/g; 890.61 mmol; 30.00 V) is added and the whole is heated at 90° C. for 1 hour. After returning to room temperature, the heterogeneous medium is concentrated under vacuum and the orange-colored solid obtained is taken up in ethyl acetate and then filtered off to give the desired product (14 g, 93%) in the form of a beige-colored solid.

b) 6-Chloro-3-iodo-1H-pyrazolo[3,4-d]pyrimidin-4-ylamine

To a solution of 6-chloro-3-iodo-1H-pyrazolo[3,4-d]pyrimidin-4-ylamine (500 mg; 1.69 mmol; 1 eq.) (2) in N,N'-dimethylformamide (7 mL) is added cesium carbonate (1.10 g; 3.38 mmol; 2 eq.) followed by 2-iodopropane (0.17 mL; 1.69 mmol; 1 eq.). The medium is stirred at 50° C. for 2 hours and, after returning to room temperature, the medium is filtered and then concentrated to dryness under vacuum. The product is purified on silica gel to give 6-chloro-3-iodo-1H-pyrazolo[3,4-d]pyrimidin-4-ylamine (160 mg, 29%) (3) in the form of a white solid.

c) 3-Iodo-1-isopropyl-$N^6$-methyl-1H-pyrazolo[3,4-d]pyrimidine-4,6-diamine

To a solution of 6-chloro-3-iodo-1-isopropyl-1H-pyrazolo[3,4-d]pyrimidin-4-ylamine (150 mg; 0.44 mmol; 2 eq.) (3) in 1,4-dioxane (1 mL) is added methylamine in methanol (555.47 µl; 2.00 M; 1.11 mmol; 5 eq.) and the whole is stirred at 85° C. After cooling the medium, the whole is concentrated under vacuum. The crude product is chromatographed on silica gel (25 g, solid deposition, heptane/ethyl acetate eluent from 45% to 85% of ethyl acetate) to give 3-iodo-1-isopropyl-$N^6$-methyl-1H-pyrazolo[3,4-d]pyrimidine-4,6-diamine (65 mg; 88%) (4) in the form of a white solid.

d) 3-(2-Aminobenzoxazol-5-yl)-1-isopropyl-$N^6$-methyl-1H-pyrazolo[3,4-d]pyrimidine-4,6-diamine To a solution of 3-iodo-1-isopropyl-$N^6$-methyl-1H-pyrazolo[3,4-d]pyrimidine-4,6-diamine (65 mg; 0.20 mmol; 1 eq.) (4) is added 1,1'-bis(diphenylphosphino)ferrocenepalladium(II) dichloride, dichloromethane (16 mg; 0.02 mmol; 0.10 eq.), 5-(4,4,5,5-tetramethyl-1,3,2-dioxaborolan-2-yl)benzo[d]oxazol-2-amine (76.35 mg; 0.29 mmol; 1.5 eq.) and aqueous 2M potassium carbonate solution (0.29 mL; 2.00 M; 0.59 mmol; 3 eq.) in 1,4-dioxane (650.00 µl). The reaction medium is heated at 100° C. for 1 hour. After total conversion, the medium is cooled and then concentrated under vacuum, followed directly by chromatography on silica gel (12 g, solid deposition, dichloromethane/methanol eluent from 3% to 10% of methanol). 3-(2-Aminobenzoxazol-5-yl)-1-isopropyl-$N^6$-methyl-1H-pyrazolo[3,4-d]pyrimidine-4,6-diamine (40 mg; 59%) (5) is obtained in the form of an ochre-colored solid.

1H NMR (DMSO-d6) δ: 1.44 (d, J=6.7 Hz, 6H), 2.82 (d, J=4.7 Hz, 3H), 4.73-4.99 (m, 1H), 6.53 (s, 1H), 7.20 (dd, J=8.2, 1.7 Hz, 1H), 7.37 (d, J=1.7 Hz, 1H), 7.43 (d, J=8.2 Hz, 1H), 7.51 (s, 2H)

MS (ESI) m/z=339 [M+H]$^+$

Example 27: 5-(6-amino-4-methyl-1-neopentyl-1H-pyrazolo[3,4-d]pyrimidin-3-yl)benzo[d]oxazol-2-amine This compound may be obtained according to the process presented in FIG. 4.

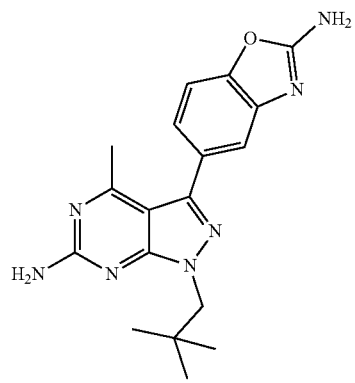 [SMILES: Cc1nc(N)nc2c1c(-c1ccc3oc(N)nc3c1)nn2CC(C)(C)C]

1H NMR (DMSO-d6) δ: 1H NMR (600 MHz, DMSO-d6, 300K) 6 ppm 7.47 (s, 2H) 7.36-7.43 (m, 2H) 7.21 (dd, J=8.1, 1.4 Hz, 1H) 6.72 (s, 2H) 4.01 (s, 2H) 2.36 (br s, 3H) 0.97 (s, 9H)

MS (ESI) m/z=352 [M+H]$^+$

Example 28: 3-(2-cyclopropylaminobenzoxazol-5-yl)-1-isopropyl-1H-pyrazolo[3,4-d]pyrimidine-4,6-diamine

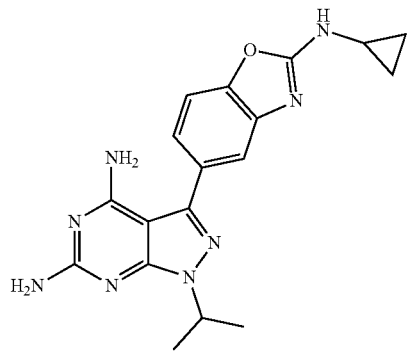 [SMILES: CC(C)n1nc(-c2ccc3oc(NC4CC4)nc3c2)c2c(N)nc(N)nc21]

1H NMR (DMSO-d6) δ: 0.56-0.60 (m, 2H), 0.73-0.77 (m, 2H), 1.42 (d, J=6.7 Hz, 6H), 2.76 (m, 1H), 4.82 (spt, J=6.7 Hz, 1H), 6.11 (brs, 4H), 7.22 (dd, J=8.1, 1.8 Hz, 1H), 7.43 (dd, J=1.8, 0.4 Hz, 1H), 7.46 (dd, J=8.1, 0.4 Hz, 1H), 8.26 (d, J=2.7 Hz, 1H).

MS (ESI) m/z=365 [M+H]$^+$

Example 29: 3-(2-amino-7-methylbenzoxazol-5-yl)-1-(2,2-dimethylbutyl)-1H-pyrazolo[3,4-d]pyrimidine-4,6-diamine

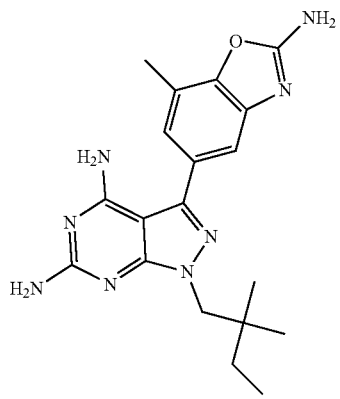 [SMILES: CCC(C)(C)Cn1nc(-c2cc(C)c3oc(N)nc3c2)c2c(N)nc(N)nc21]

1H NMR (DMSO-d6) δ: 0.90 (d, J=10.0 Hz, 9H), 1.32 (q, J=7.5 Hz, 2H), 2.42 (s, 3H), 3.93 (s, 2H); 6.11 (s, 2H), 7.03 (s, 1H), 7.18 (d, J=1.5 Hz, 1H), 7.47 (s, 2H)

MS (ESI) m/z=381 [M+H]$^+$

Example 30: 3-(2-aminobenzoxazol-5-yl)-1-(1-methylcyclobutylmethyl)-1H-pyrazolo[3,4-d]pyrimidine-4,6-diamine

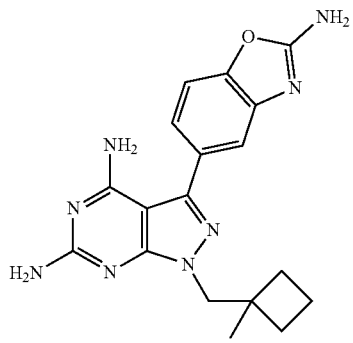 [SMILES: CC1(Cn2nc(-c3ccc4oc(N)nc4c3)c3c(N)nc(N)nc32)CCC1]

1H NMR (DMSO-d6) δ: 1.12 (s, 3H), 1.59-1.76 (m, 3H), 1.77-1.91 (m, 1H), 2.12-2.24 (m, 2H), 4.09 (s, 2H), 6.14 (s, 4H), 7.20 (dd, J=8.2, 1.8 Hz, 1H), 7.37 (d, J=1.7 Hz, 1H), 7.44 (d, J=8.2 Hz, 1H), 7.50 (s, 2H).
MS (ESI) m/z=365 [M+H]⁺

Figure 5:
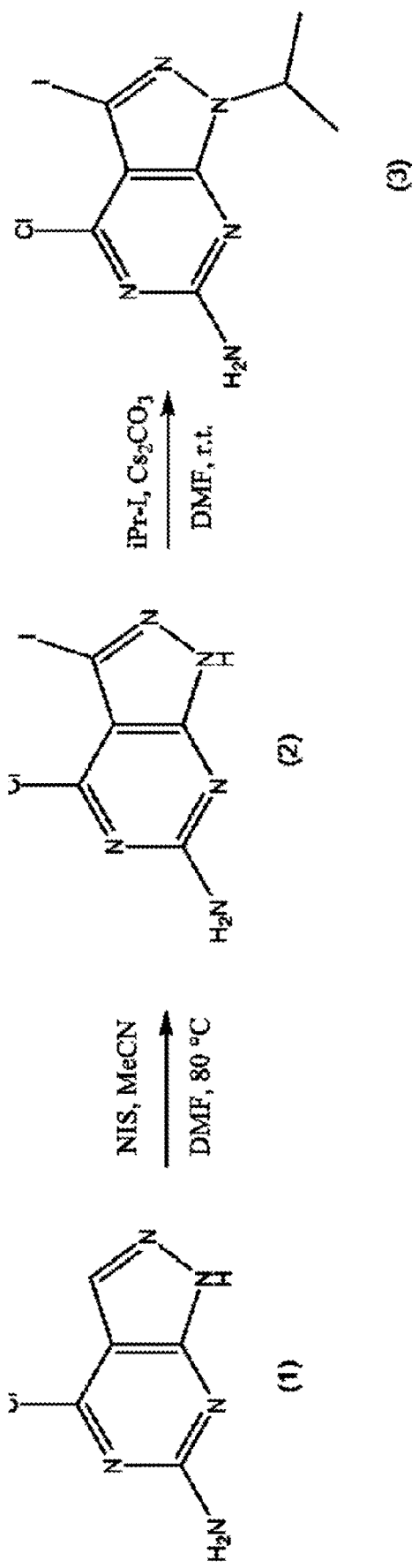
FIG. 5 represents a route for synthesizing the compound 5-(6-amino-4-chloro-1-isopropyl-1H-pyrazolo[3,4-d]pyrimidin-3-yl)benzo[d]oxazol-2-amine (example 31)

Example 31: 5-(6-Amino-4-chloro-1-isopropyl-1H-pyrazolo[3,4-d]pyrimidin-3-yl)benzo[d]oxazol-2-amine This compound may be obtained according to the process presented in FIG. 5.

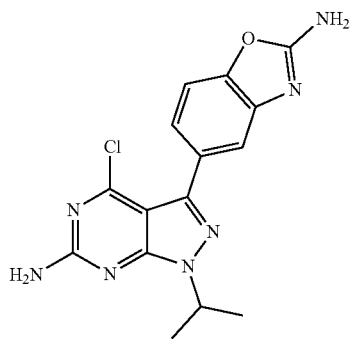 [SMILES: CC(C)n1nc(-c2ccc3oc(N)nc3c2)c2c(Cl)nc(N)nc21]

a) 4-Chloro-3-iodo-1H-pyrazolo[3,4-d]pyrimidin-6-ylamine

To a solution of 4-chloro-1H-pyrazolo[3,4-d]pyrimidin-6-ylamine (4.00 g; 23.59 mmol; 1.00 eq.) (1) in acetonitrile (60.0 mL) and DMF (4.00 mL) is added N-iodosuccinimide (10.61 g; 47.18 mmol; 2.00 eq.) at room temperature. The mixture is then heated at 80° C. for 5 days. The reaction medium is concentrated under vacuum. The medium is dissolved in a solution of NaOH (1M) and MeTHF (30 mL). The aqueous phase is extracted with MeTHF (5 mL). The organic phases are combined, dried (MgSO₄) and concentrated, and the residue is triturated with Et₂O to give 4-chloro-3-iodo-1H-pyrazolo[3,4-d]pyrimidin-6-ylamine (4.52 g, 65%) (2) in the form of a beige-colored solid. 1H NMR (DMSO-d6) δ: 7.28-7.40 (brs, 2H), 13.5 (s, 1H)
MS (ESI) m/z=295.77 [M+H]⁺ b) 4-chloro-3-iodo-1-isopropyl-1H-pyrazolo[3,4-d]pyrimidin-6-ylamine

4-Chloro-3-iodo-1H-pyrazolo[3,4-d]pyrimidin-6-ylamine (2.54 g; 8.60 mmol; 1.00 eq.) (2) is dissolved in DMF (50.0 mL) and cesium carbonate (2.80 g; 8.60 mmol; 1.00 eq.) is added, followed by 2-iodopropane (0.86 mL; 8.60 mmol; 1.00 eq.). The reaction mixture is stirred at room temperature for 3 hours 30 minutes. Water is added to the medium, which is then extracted with EtOAc. The organic phase collected is washed, dried (MgSO₄) and concentrated under vacuum. The crude product is purified by preparative LCMS (C18 column, eluent: acetonitrile in water/0.1% of formic acid) to give 4-chloro-3-iodo-1-isopropyl-1H-pyrazolo[3,4-d]pyrimidin-6-ylamine (623.00 mg; 21.47%) (3) in the form of a beige-colored solid.
1H NMR (DMSO-d₆) δ: 1.40-1.42 (d, J=6 Hz, 6H), 4.74-4.86 (h, J=6 Hz, 1H), 7.39 (brs, 2H), 13.5 (s, 1H)
MS (ESI) m/z=337.85 [M+H]⁺ c) 5-(6-Amino-4-chloro-1-isopropyl-1H-pyrazolo[3,4-d]pyrimidin-3-yl)benzo[d]oxazol-2-amine A 6 mL microwave tube is charged with 4-chloro-3-iodo-1-isopropyl-1H-pyrazolo[3,4-d]pyrimidin-6-ylamine (0.50 g; 1.48 mmol; 1.00 eq.) and 5-(4,4,5,5-tetramethyl-1,3,2-dioxaborolan-2-yl)benzo[d]oxazol-2-amine (0.58 g; 2.22 mmol; 1.50 eq.) in 1,4-dioxane (5.28 ml), followed by aqueous potassium carbonate solution (2.22 ml; 2.00 M; 4.44 mmol; 3.00 eq.), the mixture is then degassed under nitrogen three times and 1,1'-bis(diphenylphosphino)ferrocenepalladium(II) dichloride dichloromethane (120.96 mg; 0.15 mmol; 0.10 eq.) is then added rapidly. The reaction medium is heated for 1 hour at 100° C. by microwave, cooled to room temperature, dissolved in EtOAc (10 mL), filtered and concentrated to dryness. The residue obtained is purified by preparative LCMS (C18 column, eluent: acetonitrile in water/0.1% of formic acid) to give 5-(6-amino-4-chloro-1-isopropyl-1H-pyrazolo[3,4-d]pyrimidin-3-yl)benzo[d]oxazol-2-amine (0.21 g, 41%) in the form of a white crystalline solid.
1H NMR (DMSO-d6) δ: 1.47 (d, J=6.7 Hz, 6H), 4.91 (p, J=6.7 Hz, 1H), 7.22-7.32 (m, 3H), 7.41 (d, J=8.2 Hz, 1H), 7.44-7.50 (m, 3H)
MS (ESI) m/z=344 [M+H]⁺

Example 32: Enzymatic mTOR and Cellular mTORC1/mTORC2 Activities

32.1 Inhibitory Activity on mTOR Kinase

The model for screening the inhibitory activity of the molecules on mTOR was developed with the LANTHASCREEN™ technology (Lifetechnologies). The reaction substrate (400 nM final), the serial dilutions of the molecules (1% DMSO final) and the enzyme (<1 nM) are successively added to a 384-well plate (Corning 4514) in a final volume of 10 μL per well. After 1 hour of reaction at room temperature, 10 μL of a solution containing 10 mM final of EDTA and 2 nM final of terbium-labeled antibodies are added. After at least 30 minutes of incubation at room temperature, the TR-FRET signal is measured with a suitable microplate reader according to the supplier's recommendations. The data are normalized with positive controls ("POS" containing a saturating concentration of reference inhibitor) and negative controls ("NEG" containing 1% DMSO): % inhibition=((X-NEG)*100)/(POS-NEG). The IC50 values are calculated using a 4-parameter logistic model with the aid of the XLFit software (IDBS).

32.2 mTORC1/mTORC2 Inhibitory Activity

A431 cells are seeded in whole medium (DMEM+10% FCS) at 25 000 cells per well in a 96-well plate coated with poly-L-lysine. 24 hours before the experiment, the medium is replaced with serum-free medium. The serial dilutions of the test molecules are added (0.1% DMSO final). After incubation for 3 hours at 37° C., the phosphorylation of the biomarkers S6RP (mTORC1) and AKT (mTORC2) is measured using the HTRF technology (Cisbio) according to the supplier's recommendations. The data are normalized with positive controls ("POS" containing a saturating concentration of reference inhibitor) and negative controls ("NEG" containing 1% DMSO): % inhibition=((X-NEG)*100)/(POS-NEG). The IC50 values are calculated using a 4-parameter logistic model with the aid of the XLFit software (IDBS).

| | Table of the activity results: | | | |
|---|---|---|---|---|
| Example | Chemical name | Ki mTOR (nM) | IC50 mTORC1 (nM) | IC50 mTORC2 (nM) |
| 1 | 3-(2-aminobenzoxazol-5-yl)-1-((S)-1,3-dimethylbutyl)-1H-pyrazolo[3,4-d]pyrimidine-4,6-diamine | 0.8 | 1.0 | 1.5 |
| 2 | 3-(2-amino-6-fluorobenzoxazol-5-yl)-1-((S)-1,3-dimethylbutyl)-1H-pyrazolo[3,4-d]pyrimidine-4,6-diamine | 1.0 | 1.2 | 2.1 |
| 3 | 3-(2-amino-4-fluorobenzoxazol-5-yl)-1-(1-methylcyclobutylmethyl)-1H-pyrazolo[3,4-d]pyrimidine-4,6-diamine | 0.3 | 0.2 | 1.0 |
| 4 | 3-(2-amino-6-fluorobenzoxazol-5-yl)-1-(1-methylcyclobutylmethyl)-1H-pyrazolo[3,4-d]pyrimidine-4,6-diamine | 1.4 | 1.3 | 3.4 |
| 5 | 3-(2-amino-4-fluorobenzoxazol-5-yl)-1-((S)-1,3-dimethylbutyl)-1H-pyrazolo[3,4-d]pyrimidine-4,6-diamine | 0.4 | 0.5 | 1.1 |
| 6 | N-(5-(4,6-diamino-1-(2,2-dimethylbutyl)-1H-pyrazolo[3,4-d]pyrimidin-3-yl)benzo[d]oxazole-2-yl)acetamide | 0.5 | 0.7 | 5.9 |
| 7 | 3-(2-aminobenzoxazol-5-yl)-1-(2,2-dimethylpropyl)-1H-pyrazolo[3,4-d]pyrimidine-4,6-diamine | 0.6 | 0.7 | 2.4 |
| 8 | 3-(2-aminobenzoxazol-5-yl)-1-(2,2-dimethylbutyl)-1H-pyrazolo[3,4-d]pyrimidine-4,6-diamine | 0.6 | 1.2 | 3.0 |
| 9 | 3-(2-aminobenzoxazol-5-yl)-1-(3-methylthietan-3-ylmethyl)-1H-pyrazolo[3,4-d]pyrimidine-4,6-diamine | 0.6 | 1.0 | 2.8 |
| 10 | 3-(2-amino-4-fluorobenzoxazol-5-yl)-1-(2,2-dimethylbutyl)-1H-pyrazolo[3,4-d]pyrimidine-4,6-diamine | 0.8 | 0.2 | 1.2 |
| 11 | 1-(2,2-dimethylpropyl)-3-(2-ethylaminobenzoxazol-5-yl)-1H-pyrazolo[3,4-d]pyrimidine-4,6-diamine | 0.8 | 5.0 | 5.9 |
| 12 | 3-(2-aminobenzoxazol-5-yl)-1-(2,2-dimethylbut-3-enyl)-1H-pyrazolo[3,4-d]pyrimidine-4,6-diamine | 1.2 | 1.1 | 3.7 |
| 13 | (+)-3-(2-aminobenzoxazol-5-yl)-1-((S)-2-methyl-2-tetrahydrofuran-2-ylpropyl)-1H-pyrazolo[3,4-d]pyrimidine-4,6-diamine | 1.2 | 1.4 | 4.1 |
| 14 | 3-(2-aminobenzoxazol-5-yl)-1-(2,2-dimethylbut-3-ynyl)-1H-pyrazolo[3,4-d]pyrimidine-4,6-diamine | 1.2 | 1.2 | 3.8 |
| 15 | 3-[4,6-diamino-3-(2-aminobenzoxazol-5-yl)pyrazolo[3,4-d]pyrimidin-1-yl]-2,2-dimethylpropan-1-ol | 1.5 | 1.7 | 7.2 |
| 16 | 3-(2-aminobenzoxazol-5-yl)-1-(2-methyl-2-methylsulfanylpropyl)-1H-pyrazolo[3,4-d]pyrimidine-4,6-diamine | 1.7 | 2.2 | 10.2 |
| 17 | 3-(2-amino-4-chlorobenzoxazol-5-yl)-1-(2,2-dimethylpropyl)-1H-pyrazolo[3,4-d]pyrimidine-4,6-diamine | 1.8 | 1.2 | 4.0 |
| 18 | 3-(2-amino-6-methoxybenzoxazol-5-yl)-1-(2,2-dimethylpropyl)-1H-pyrazolo[3,4-d]pyrimidine-4,6-diamine | 2.1 | 2.1 | 4.3 |

-continued

Table of the activity results:

| Example | Chemical name | Ki mTOR (nM) | IC50 mTORC1 (nM) | IC50 mTORC2 (nM) |
|---|---|---|---|---|
| 19 | 2-[4,6-diamino-1-(2,2-dimethylpropyl)-1H-pyrazolo[3,4-d]pyrimidin-3-yl]-1H-pyrrolo[2,3-b]pyridin-5-ol | 2.3 | 27.4 | 65.5 |
| 20 | 3-(2-amino-6-methoxybenzoxazol-5-yl)-1-(2,2-dimethylbutyl)-1H-pyrazolo[3,4-d]pyrimidine-4,6-diamine | 2.9 | 2.1 | 7.0 |
| 21 | 3-(2-aminobenzoxazol-5-yl)-1-isopropyl-1H-pyrazolo[3,4-d] pyrimidine-4,6-diamine | 3.8 | 3.8 | 10.7 |
| 22 | 3-(2-aminobenzoxazol-5-yl)-1-(2-ethyl-2-methanesulfonylbutyl)-1H-pyrazolo[3,4-d]pyrimidine-4,6-diamine | 3.9 | 10.2 | 26.6 |
| 23 | 3-(2-aminobenzoxazol-5-yl)-4-chloro-1-isobutyl-1H-pyrazolo[3,4-d]pyrimidin-6-ylamine | 5.8 | 2.8 | 5.9 |
| 24 | 3-(2-aminobenzoxazol-5-yl)-1-isopropyl-1H-pyrazolo[3,4-d]pyrimidin-6-ylamine | 6.1 | 6.8 | 15.5 |
| 25 | 3-(2-amino-6-chlorobenzoxazol-5-yl)-1-((S)-1,2-dimethylpropyl)-1H-pyrazolo[3,4-d]pyrimidine-4,6-diamine | 8.1 | 4.5 | 13.1 |
| 26 | 3-(2-aminobenzoxazol-5-yl)-1-isopropyl-N*6*-methyl-1H-pyrazolo[3,4-d]pyrimidine-4,6-diamine | 13.4 | 29.7 | 62.2 |
| 27 | 5-(6-amino-4-methyl-1-neopentyl-1H-pyrazolo[3,4-d]pyrimidin-3-yl)benzo[d]oxazol-2-amine | 14.3 | 8.1 | 15.3 |
| 28 | 3-(2-cyclopropylaminobenzoxazol-5-yl)-1-isopropyl-1H-pyrazolo[3,4-d] pyrimidine-4,6-diamine | 21.0 | 43.8 | 40.2 |
| 29 | 3-(2-amino-7-methylbenzoxazol-5-yl)-1-(2,2-dimethylbutyl)-1H-pyrazolo[3,4-d]pyrimidine-4,6-diamine | 102.2 | 233.6 | 745.7 |
| 30 | 3-(2-aminobenzoxazol-5-yl)-1-(1-methylcyclobutylmethyl)-1H-pyrazolo[3,4-d]pyrimidine-4,6-diamine | 0.58 | 0.87 | 2.7 |
| 31 | 5-(6-Amino-4-chloro-1-isopropyl-1H-pyrazolo[3,4-d]pyrimidin-3-yl)benzo[d]oxazol-2-amine | 10 | 8.4 | 21 |

IC50: inhibitor concentration causing 50% inhibition.
This is a practical indicator of efficacy.
Ki: dissociation constant of the enzyme-inhibitor complex. This indicates the affinity between the enzyme and the inhibitor (in an inverse manner).

The affinity of an inhibitor for an enzyme is given by the inhibition constant Ki, which represents the inhibitor concentration for which half of the enzymatic sites are occupied. Thus, the affinity of an inhibitor is proportionately greater the smaller the Ki. This inhibition constant, expressed in moles per liter, also corresponds to the dissociation constant of the enzyme-inhibitor complex.

Taking the above results into consideration, the compounds with activities (IC50 mTORC1 and/or IC50 mTORC2) of less than 5 nM are more particularly preferred.

Example 33: Chronogram of a Patch Model of Atopic Dermatitis in Mice

Figure 6:
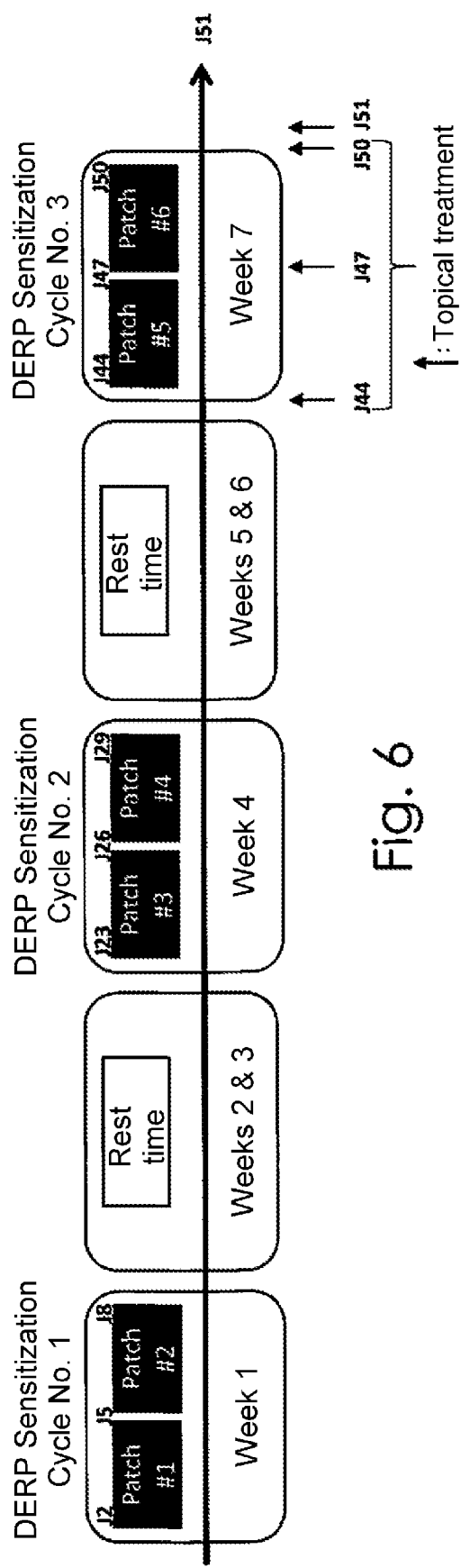
FIG. 6 represents a chronogram of a patch model of atopic dermatitis in mice according to example 33.

As illustrated in FIG. 6, female Balb/c mice were treated with the allergen *Dermatophagoides pteronyssinus* (DERP) in the course of three cycles of epicutaneous (patch) sensitization on the abdominal skin with two patches applied twice a week followed by two weeks of rest, for seven weeks. The antagonist (mTOR inhibitor) according to example 31 tested was formulated at 0.07% in an acetone vehicle, applied to the skin of the back of the mouse (10 μl/ear on the two faces) and left for 2 hours before applying the DERP patches. Topical treatments with the antagonist (mTOR inhibitor) or a corticosteroid (betamethasone 17-valerate at 0.01% used as control) were performed only three times in the course of the third and final week of sensitization (on days 44, 47 and 50).

Example 34: Transepidermal Water Loss (or TEWL) Test in a Patch Model of Atopic Dermatitis after Application of an mTOR Antagonist The treatment protocol is illustrated in FIG. 6.
The transepidermal water loss TEWL is measured using a TEWAMETER® on a control animal. The TEWAMETER® probe measures the density gradient of water evaporation from the skin indirectly by means of two pairs of sensors (temperature and relative humidity) inside a hollow cylinder. A microprocessor analyzes the values and expresses the evaporation rate in g/h/m2.

Figures 7, 8, 9:
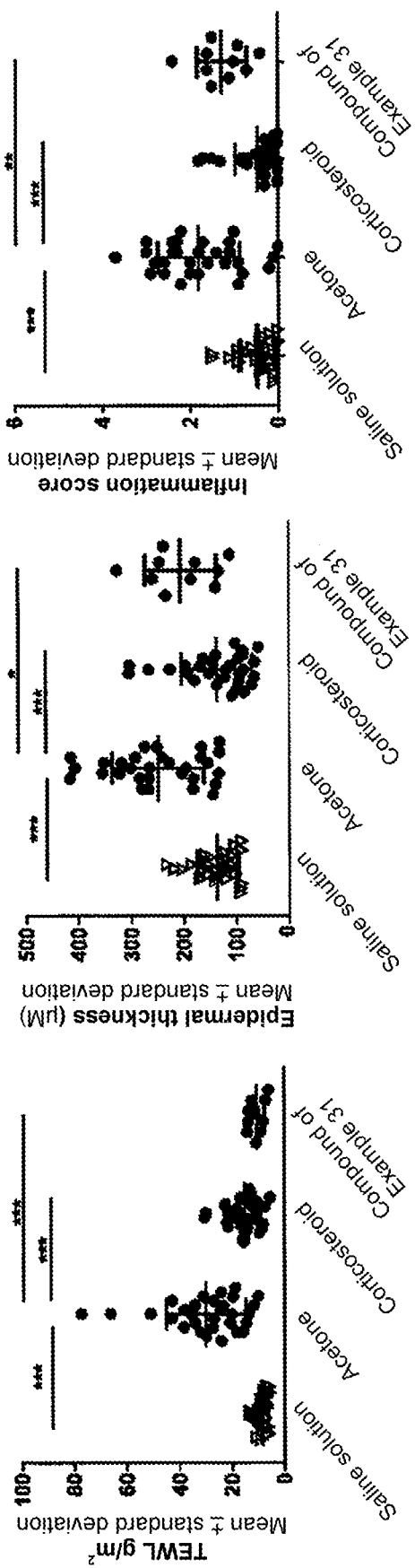
FIG. 7 represents the transepidermal water loss (or TEWL) test results in a patch model of atopic dermatitis after application of an mTOR antagonist according to example 34.
FIG. 8 represents the epidermal thickness in a patch model of atopic dermatitis after application of an mTOR antagonist according to example 35.
FIG. 9 represents the inflammation score in a patch model of atopic dermatitis after application of an mTOR antagonist according to example 36.

The results obtained are illustrated in FIG. 7.

Example 35: Epidermal Thickness in a Patch Model of Atopic Dermatitis after Application of an mTOR Antagonist The treatment protocol is illustrated in FIG. 6.

The epidermal thickness is measured by histological morphometric analyses on sections 6 µm thick stained with HE using skin samples fixed beforehand with physiological saline.

The results obtained are illustrated in FIG. 8.

Example 36: Inflammation Score in a Patch Model of Atopic Dermatitis after Application of an mTOR Antagonist The treatment protocol is illustrated in FIG. 6.

The inflammation score is defined visually as a function of predefined scales of dryness, cutaneous eruption, baldness, excoriation and lichenification. The mean of the five scores attributed to an individual mouse on a given day gives the clinical score attributed on that specific day.

The results obtained are illustrated in FIG. 9.

Example 37: Study of an mTOR Antagonist According to the Invention in a Patch Model of Atopic Dermatitis (AD)

To evaluate the contribution of mTOR to the inflammatory response of atopic dermatitis, the inventors used an atopic dermatitis model described previously based on repeated epicutaneous sensitizations (Spergel et al. JCI 1998; Staumont-Sallé et al. JEM 2015), with *Dermatophagoides pteronyssinus* (DERP) as antigen. In this model, the skin lesions caused by the atopic dermatitis present inflammation with Th2 dominant characterized by dermal infiltration of CD4+T lymphocytes and of eosinophils accompanied by deposition of eosinophil products and an increase in the cutaneous expression of the Th2 cytokines.

Following the protocol of example 33, the inflammatory response of atopic dermatitis was provoked by epicutaneous sensitization with patches soaked with 100 µg of allergen in sterile saline solution (*Dermatophagoides pteronyssinus* or DERP) or with a vehicle applied to the abdominal skin 24 hours after shaving and left in place for three periods of one week (with renewal of the patch in the middle of the week), with a 2-week interval between the applications. The presence of the patches and of a transparent occlusive dressing on top prevented the mice from licking, biting and scratching; consequently, the inflammatory response in this model is not due to the itching cycle.

The antagonist according to example 31 (mTOR inhibitor) was formulated at 0.07% in an acetone-based vehicle, applied to the sensitized skin 2 hours before installation of the DERP patches. Topical treatments with the antagonist according to the invention or a corticosteroid (used as control) were performed only three times in the course of the third and final week of sensitization (on days 44, 47 and 50).

At the time of removal of the last patch (day 51), skin samples were collected for histological and immunohistological analyses. FIG. 6 shows the treatment chronogram.

The results are presented in FIGS. 7 to 9. The antagonist according to example 31 (mTOR inhibitor) reduces all the parameters studied.

The increase in the rate of transepidermal water loss TEWL, a clinical sign of dysfunction of the skin barrier, is significantly decreased (−68%).

Another parameter of skin barrier dysfunction, epidermal acanthosis, is partially restored with the mTOR antagonist (−39% respectively on the epidermal thickness).

The inflammatory parameters are also impacted, such as the inflammatory scores (−40).

The efficacy of an mTOR antagonist (mTOR inhibitor) according to the invention is quite similar to treatment with corticosteroid.

The Applicant has now discovered, surprisingly, that, in a murine model of atopic dermatitis which is not due to itching, the mTOR antagonists (mTOR inhibitors) significantly decrease the clinical signs (such as the clinical scores and the transepidermal water loss or TEWL) and the histological parameters (such as the number of inflammatory cells in the dermis and the epidermal thickness).

The invention claimed is:
1. A compound of formula (I):

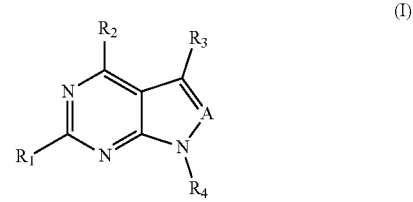

or a pharmaceutically acceptable salt or stereoisomer thereof,
wherein:
A represents N;
$R_1$ represents $NH_2$;
$R_2$ represents F, Cl, Br, I, or $NH_2$;
$R_3$ represents a fused, bicyclic heteroaryl, wherein the fused, bicyclic heteroaryl is optionally substituted with one or more substituents independently selected from the group consisting of F, Cl, Br, I, CN, $CH_3$, $CH_2CH_3$, $CF_3$, $NHR_5$, and $OR_6$;
$R_4$ represents $C_3$-$C_{10}$ alkyl or $C_3$-$C_{10}$ carbocyclyl;
wherein the $C_3$-$C_{10}$ alkyl is branched;
wherein the $C_3$-$C_{10}$ carbocyclyl is optionally bicyclic;
wherein the $C_3$-$C_{10}$ alkyl or $C_3$-$C_{10}$ carbocyclyl is optionally interrupted with one heteroatom selected from the group consisting of O and S; and
wherein the $C_3$-$C_{10}$ alkyl or $C_3$-$C_{10}$ carbocyclyl is optionally substituted with one or more substituents independently selected from the group consisting of F, $C_3$-$C_6$ cycloalkyl, and heterocycloalkyl;
$R_5$ represents H, $C_1$-$C_6$ alkyl, acyl, or cyclopropyl;
wherein the $C_1$-$C_6$ alkyl is saturated or unsaturated;
wherein the $C_1$-$C_6$ alkyl is optionally interrupted with one heteroatom selected from the group consisting of O and S; and
wherein the $C_1$-$C_6$ alkyl is optionally substituted with one substituent selected from the group consisting of $C_3$-$C_5$ cycloalkyl and heterocycloalkyl; and
$R_6$ represents H or $CH_3$.

2. The compound according to claim 1, or a pharmaceutically acceptable salt or stereoisomer thereof, wherein $R_2$ represents Cl or $NH_2$.

3. The compound according to claim 2, wherein the compound is of formula (Ia):

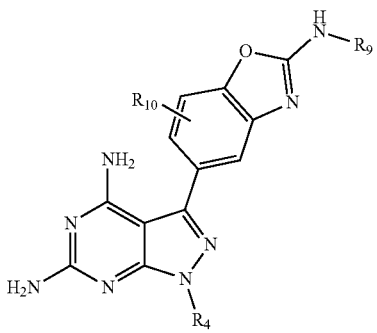

or a pharmaceutically acceptable salt or stereoisomer thereof,
wherein:
$R_9$ represents H, $CH_3$, or $CH_2CH_3$; and
each $R_{10}$ independently represents H, F, Cl, $CH_3$, OH, or $OCH_3$.

4. The compound according to claim 3, or a pharmaceutically acceptable salt or stereoisomer thereof, wherein:
$R_4$ represents $C_3$-$C_{10}$ alkyl, wherein the $C_3$-$C_{10}$ alkyl is branched;
$R_9$ represents H; and
each $R_{10}$ independently represents H, F, Cl, or $CH_3$.

5. The compound according to claim 4, or a pharmaceutically acceptable salt or stereoisomer thereof, wherein:
$R_4$ represents $C_4$-$C_6$ alkyl, wherein the $C_4$-$C_6$ alkyl is branched; and
each $R_{10}$ independently represents H or F.

6. A pharmaceutical composition comprising a compound according to claim 1, or a pharmaceutically acceptable salt or stereoisomer thereof, in a physiologically acceptable medium.

7. The pharmaceutical composition according to claim 6, wherein the pharmaceutical composition is formulated for oral administration or topical administration.

8. The pharmaceutical composition according to claim 7, wherein the pharmaceutical composition is formulated for topical administration.

9. The pharmaceutical composition according to claim 6, wherein the pharmaceutical composition comprises the compound, or a pharmaceutically acceptable salt or stereoisomer thereof, in an amount in the range of 0.001% (w/w) to 5% (w/w).

10. A method for inhibiting mammalian target of rapamycin (mTOR) activity in a subject, wherein the method comprises administering to the subject in need thereof a therapeutically effective amount of the pharmaceutical composition according to claim 6.

11. The method according to claim 10, wherein the subject suffers from a dermatological complaint associated with a keratinization disorder.

12. The method according to claim 11, wherein the keratinization disorder has a component selected from the group consisting of an inflammatory component, a proliferative component, and an immunoallergic component, or a combination thereof.

13. The method according to claim 11, wherein the dermatological complaint associated with a keratinization disorder is selected from the group consisting of acne, actinic keratosis, atopic dermatitis, and psoriasis.

14. The method according to claim 13, wherein the dermatological complaint associated with a keratinization disorder is atopic dermatitis.

15. The method according to claim 14, wherein the atopic dermatitis has an inflammatory component.

16. The method according to claim 14, wherein the method further comprises reinforcing the barrier function in the subject suffering from atopic dermatitis.

17. A compound selected from the group consisting of:
5-(6-amino-4-chloro-1-isopropyl-1H-pyrazolo[3,4-d]pyrimidin-3-yl)benzo[d]oxazol-2-amine;
3-(2-aminobenzoxazol-5-yl)-4-chloro-1-isobutyl-1H-pyrazolo[3,4-d]pyrimidin-6-ylamine;
3-(2-aminobenzoxazol-5-yl)-1-isopropyl-1H-pyrazolo[3,4-d]pyrimidine-4,6-diamine;
3-(2-cyclopropylaminobenzoxazol-5-yl)-1-isopropyl-1H-pyrazolo[3,4-d]pyrimidine-4,6-diamine;
3-(2-aminobenzoxazol-5-yl)-1-(2,2-dimethylpropyl)-1H-pyrazolo[3,4-d]pyrimidine-4,6-diamine;
3-(2-aminobenzoxazol-5-yl)-1-((S)-1,3-dimethylbutyl)-1H-pyrazolo[3,4-d]pyrimidine-4,6-diamine;
3-(2-aminobenzoxazol-5-yl)-1-(2,2-dimethylbutyl)-1H-pyrazolo[3,4-d]pyrimidine-4,6-diamine;
1-(2,2-dimethylpropyl)-3-(2-ethylaminobenzoxazol-5-yl)-1H-pyrazolo[3,4-d]pyrimidine-4,6-diamine;
3-(2-amino-4-fluorobenzoxazol-5-yl)-1-((S)-1,3-dimethylbutyl)-1H-pyrazolo[3,4-d]pyrimidine-4,6-diamine;
3-(2-amino-6-fluorobenzoxazol-5-yl)-1-((S)-1,3-dimethylbutyl)-1H-pyrazolo[3,4-d]pyrimidine-4,6-diamine;
3-(2-amino-6-chlorobenzoxazol-5-yl)-1-((S)-1,2-dimethylpropyl)-1H-pyrazolo[3,4-d]pyrimidine-4,6-diamine;
3-(2-amino-4-chlorobenzoxazol-5-yl)-1-(2,2-dimethylpropyl)-1H-pyrazolo[3,4-d]pyrimidine-4,6-diamine;
3-(2-amino-6-methoxybenzoxazol-5-yl)-1-(2,2-dimethylpropyl)-1H-pyrazolo[3,4-d]pyrimidine-4,6-diamine;
3-(2-amino-6-methoxybenzoxazol-5-yl)-1-(2,2-dimethylbutyl)-1H-pyrazolo[3,4-d]pyrimidine-4,6-diamine;
3-(2-amino-7-methyl-benzoxazol-5-yl)-1-(2,2-dimethylbutyl)-1H-pyrazolo[3,4-d]pyrimidine-4,6-diamine;
2-[4,6-diamino-1-(2,2-dimethylpropyl)-1H-pyrazolo[3,4-d]pyrimidin-3-yl]-1H-pyrrolo[2,3-b]pyridin-5-ol;
3-(2-amino-4-fluorobenzoxazol-5-yl)-1-(2,2-dimethylbutyl)-1H-pyrazolo[3,4-d]pyrimidine-4,6-diamine;
N-(5-(4,6-diamino-1-(2,2-dimethylbutyl)-1H-pyrazolo[3,4-d]pyrimidin-3-yl)benzo[d]oxazol-2-yl)acetamide;
3-(2-aminobenzoxazol-5-yl)-1-isopropyl-1H-pyrazolo[3,4-d]pyrimidin-6-ylamine;
5-(6-amino-4-methyl-1-neopentyl-1H-pyrazolo[3,4-d]pyrimidin-3-yl)benzo[d]oxazol-2-amine;
3-(2-aminobenzoxazol-5-yl)-1-(1-methylcyclobutylmethyl)-1H-pyrazolo[3,4-d]pyrimidine-4,6-diamine;
3-(2-amino-4-fluorobenzoxazol-5-yl)-1-(1-methylcyclobutylmethyl)-1H-pyrazolo[3,4-d]pyrimidine-4,6-diamine;
3-(2-amino-6-fluorobenzoxazol-5-yl)-1-(1-methylcyclobutylmethyl)-1H-pyrazolo[3,4-d]pyrimidine-4,6-diamine;
3-(2-aminobenzoxazol-5-yl)-1-(3-methylthietan-3-ylmethyl)-1H-pyrazolo[3,4-d]pyrimidine-4,6-diamine;
(+)-3-(2-aminobenzoxazol-5-yl)-1-((S)-2-methyl-2-tetrahydrofuran-2-ylpropyl)-1H-pyrazolo[3,4-d]pyrimidine-4,6-diamine;

3-[4,6-diamino-3-(2-aminobenzoxazol-5-yl)pyrazolo[3,4-d]pyrimidin-1-yl]-2,2-dimethylpropan-1-ol;

3-(2-aminobenzoxazol-5-yl)-1-(2-methyl-2-methylsulfinylpropyl)-1H-pyrazolo[3,4-d]pyrimidine-4,6-diamine;

3-(2-aminobenzoxazol-5-yl)-1-(2-ethyl-2-methanesulfonylbutyl)-1H-pyrazolo[3,4-d]pyrimidine-4,6-diamine;

3-(2-aminobenzoxazol-5-yl)-1-(2,2-dimethylbut-3-enyl)-1H-pyrazolo[3,4-d]pyrimidine-4,6-diamine;

3-(2-aminobenzoxazol-5-yl)-1-(2,2-dimethylbut-3-ynyl)-1H-pyrazolo[3,4-d]pyrimidine-4,6-diamine; and 3-(2-aminobenzoxazol-5-yl)-1-isopropyl-N6-methyl-1H-pyrazolo[3,4-d]pyrimidine-4,6-diamine, or a pharmaceutically acceptable salt thereof.

* * * * *